US010800846B2

(12) United States Patent
Cuillerot et al.

(10) Patent No.: US 10,800,846 B2
(45) Date of Patent: *Oct. 13, 2020

(54) PD-1/PD-L1 INHIBITORS FOR THE TREATMENT OF CANCER

(71) Applicants: Merck Patent GmbH, Darmstadt (DE); Pfizer Inc., New York, NY (US)

(72) Inventors: Jean-Marie Cuillerot, Somerville, MA (US); Anja von Heydebreck, Darmstadt (DE); Guojun Yuan, Winchester, MA (US)

(73) Assignees: MERCK PATENT GMBH, Darmstadt (DE); PFIZER INC., New York, NY (US)

(*) Notice: Subject to any disclaimer, the term of this patent is extended or adjusted under 35 U.S.C. 154(b) by 183 days.

This patent is subject to a terminal disclaimer.

(21) Appl. No.: 15/553,437

(22) PCT Filed: Feb. 23, 2016

(86) PCT No.: PCT/US2016/019120
§ 371 (c)(1),
(2) Date: Aug. 24, 2017

(87) PCT Pub. No.: WO2016/137985
PCT Pub. Date: Sep. 1, 2016

(65) Prior Publication Data
US 2018/0244781 A1    Aug. 30, 2018

Related U.S. Application Data

(60) Provisional application No. 62/254,424, filed on Nov. 12, 2015, provisional application No. 62/215,394, filed on Sep. 8, 2015, provisional application No. 62/160,291, filed on May 12, 2015, provisional application No. 62/133,721, filed on Mar. 16, 2015, provisional application No. 62/121,025, filed on Feb. 26, 2015.

(51) Int. Cl.
*C07K 16/28* (2006.01)
*A61K 39/395* (2006.01)
*C07K 16/30* (2006.01)
*A61P 35/04* (2006.01)
*A61P 35/00* (2006.01)
*A61K 39/00* (2006.01)

(52) U.S. Cl.
CPC .......... *C07K 16/2827* (2013.01); *A61P 35/00* (2018.01); *A61P 35/04* (2018.01); *C07K 16/30* (2013.01); *A61K 2039/505* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly | |
| 5,545,806 A | 8/1996 | Lonberg | |
| 5,545,807 A | 8/1996 | Surani | |
| 5,569,825 A | 10/1996 | Lonberg | |
| 5,625,126 A | 4/1997 | Lonberg | |
| 5,633,425 A | 5/1997 | Lonberg | |
| 5,641,870 A | 6/1997 | Rinderknecht | |
| 5,661,061 A | 8/1997 | Usuami | |
| 6,075,181 A | 6/2000 | Kucherlapati | |
| 6,150,584 A | 11/2000 | Kucherlapati | |
| 6,534,524 B1 | 3/2003 | Kania | |
| 6,884,890 B2 | 4/2005 | Kania | |
| 6,982,321 B2 | 1/2006 | Winter | |
| 7,087,409 B2 | 8/2006 | Barbas | |
| 7,141,581 B2 | 11/2006 | Bender | |
| 7,232,910 B2 | 6/2007 | Ewanicki | |
| 7,326,414 B2 | 2/2008 | Bedian | |
| 7,488,802 B2 | 2/2009 | Collins | |
| 7,521,051 B2 | 4/2009 | Collins | |
| 7,794,710 B2 * | 9/2010 | Chen | A61K 39/0011 424/130.1 |
| 7,960,515 B2 | 6/2011 | Min | |
| 8,008,449 B2 | 8/2011 | Korman | |
| 8,168,757 B2 | 5/2012 | Finnefrock | |
| 8,337,850 B2 | 12/2012 | Ahrens | |
| 8,354,509 B2 | 1/2013 | Carven | |
| 8,383,796 B2 | 2/2013 | Korman | |
| 8,552,154 B2 | 10/2013 | Freeman | |
| 8,779,108 B2 | 7/2014 | Queva | |
| 8,791,140 B2 | 7/2014 | Campeta | |
| 8,993,731 B2 | 3/2015 | Tyson | |
| 9,045,545 B1 * | 6/2015 | Clube | C12Q 1/6883 |
| 9,073,994 B2 | 7/2015 | Honjo | |
| 9,457,019 B2 | 10/2016 | Flynn | |

(Continued)

FOREIGN PATENT DOCUMENTS

EP        0404097        12/1990
WO     WO1991010741      7/1991

(Continued)

OTHER PUBLICATIONS

Brahmer et al., "Safety and activity of anti-PD-L1 antibody in patients with advanced cancer", The New England Journal of Medicine, 366:2455-2465 (2012).

(Continued)

*Primary Examiner* — Ilia I Ouspenski
(74) *Attorney, Agent, or Firm* — Haley Guiliano LLP; James F. Haley, Jr.; Brian M. Gummow

(57) ABSTRACT

The invention relates to methods of treating cancer in a subject, comprising administering to the subject a therapeutically effective amount of an inhibitor of the interaction between the PD-1 receptor and its ligand PD-L1.

9 Claims, 2 Drawing Sheets

Specification includes a Sequence Listing.

(56) References Cited

U.S. PATENT DOCUMENTS

| | | | |
|---|---|---|---|
| 9,539,245 B2 | 1/2017 | Peters | |
| 9,624,298 B2* | 4/2017 | Nastri | A61K 39/3955 |
| 9,682,143 B2 | 6/2017 | Chang | |
| 9,683,048 B2 | 6/2017 | Freeman | |
| 9,765,147 B2 | 9/2017 | Wong | |
| 1,000,475 A1 | 6/2018 | Wang | |
| 9,993,551 B2 | 6/2018 | Lebwohl | |
| 10,138,299 B2* | 11/2018 | Cogswell | C07K 16/2827 |
| 10,323,092 B2* | 6/2019 | Cogswell | C07K 16/2827 |
| 10,570,202 B2 | 2/2020 | Martini | |
| 2004/0224988 A1 | 11/2004 | Freddo | |
| 2006/0091067 A1 | 5/2006 | Fan | |
| 2006/0094763 A1 | 5/2006 | Ye | |
| 2007/0203196 A1 | 8/2007 | Ewanicki | |
| 2008/0274192 A1 | 11/2008 | Friesen | |
| 2010/0179329 A1 | 7/2010 | Campeta | |
| 2012/0089541 A1 | 4/2012 | Patel | |
| 2013/0078240 A1 | 3/2013 | Ahrens | |
| 2013/0309250 A1* | 11/2013 | Cogswell | C07K 16/2827 424/172.1 |
| 2014/0242071 A1 | 8/2014 | Liu | |
| 2014/0248347 A1 | 9/2014 | Morgado | |
| 2014/0288125 A1 | 9/2014 | Murray | |
| 2014/0341917 A1* | 11/2014 | Nastri | A61K 39/3955 424/139.1 |
| 2015/0190506 A1 | 7/2015 | Cheung | |
| 2015/0210769 A1 | 7/2015 | Freeman | |
| 2015/0273033 A1* | 10/2015 | Bosch | A61K 35/15 424/144.1 |
| 2016/0009805 A1* | 1/2016 | Kowanetz | A61K 39/3955 424/134.1 |
| 2016/0083401 A1 | 3/2016 | Fuchss | |
| 2016/0108123 A1* | 4/2016 | Freeman | C07K 16/2827 424/85.2 |
| 2016/0152715 A1* | 6/2016 | Wong | C07K 16/2818 424/134.1 |
| 2016/0159905 A1 | 6/2016 | Abdiche | |
| 2017/0008971 A1 | 1/2017 | Dennis | |
| 2017/0088626 A1 | 3/2017 | Jure-Kunkel | |
| 2017/0158776 A1 | 6/2017 | Feltquate | |
| 2017/0166641 A1 | 6/2017 | Martini | |
| 2017/0209574 A1 | 7/2017 | Cao | |
| 2017/0296659 A1 | 10/2017 | Lebwohl | |
| 2017/0298106 A1 | 10/2017 | Roschke | |
| 2017/0320930 A1 | 11/2017 | Matzke-Ogi | |
| 2018/0162941 A1 | 6/2018 | Thanavala | |
| 2018/0169232 A1 | 6/2018 | Andrews | |
| 2018/0186882 A1 | 7/2018 | Freeman | |
| 2018/0282415 A1 | 10/2018 | Lin | |
| 2019/0144545 A1 | 5/2019 | Nuyten | |
| 2019/0330352 A1 | 10/2019 | Andrews | |
| 2020/0048352 A1* | 2/2020 | Zimmermann | A61N 5/00 |

FOREIGN PATENT DOCUMENTS

| | | |
|---|---|---|
| WO | WO1993011161 | 6/1993 |
| WO | WO1996033735 | 10/1996 |
| WO | WO1996034096 | 10/1996 |
| WO | WO1998024893 | 6/1998 |
| WO | WO2004072286 | 8/2001 |
| WO | WO2004004771 | 1/2004 |
| WO | WO2004056875 | 7/2004 |
| WO | WO2006048745 | 5/2006 |
| WO | WO2007005874 | 1/2007 |
| WO | WO2008100562 | 8/2008 |
| WO | WO2008156712 | 12/2008 |
| WO | WO2010027827 | 3/2010 |
| WO | WO2010036959 | 4/2010 |
| WO | WO2010077634 | 7/2010 |
| WO | WO2010089411 | 8/2010 |
| WO | WO2011066342 | 6/2011 |
| WO | WO2011068561 | 6/2011 |
| WO | WO2013019906 | 2/2013 |
| WO | WO2013028231 | 2/2013 |
| WO | WO2013046133 | 4/2013 |
| WO | 2013/079174 | 6/2013 |
| WO | WO2013119202 | 8/2013 |
| WO | WO2013164754 | 11/2013 |
| WO | WO2013181452 | 12/2013 |
| WO | WO2014100079 | 6/2014 |
| WO | WO2014163684 | 10/2014 |
| WO | WO2014167088 | 10/2014 |
| WO | WO2015036511 | 3/2015 |
| WO | WO2015061668 | 4/2015 |
| WO | WO2015069266 | 5/2015 |
| WO | WO2015088847 | 6/2015 |
| WO | WO2015095410 | 6/2015 |
| WO | WO2015095423 | 6/2015 |
| WO | WO2014151006 | 9/2015 |
| WO | WO2015134605 | 9/2015 |
| WO | WO2016014148 | 1/2016 |
| WO | WO2016032927 | 3/2016 |
| WO | WO2016059602 | 4/2016 |
| WO | WO2016081384 | 5/2016 |
| WO | WO2016089873 | 6/2016 |
| WO | WO2016100882 | 6/2016 |
| WO | WO2016137985 | 9/2016 |
| WO | WO2016205277 | 12/2016 |
| WO | WO2015036499 | 3/2017 |
| WO | WO2017197140 | 11/2017 |

OTHER PUBLICATIONS

International Search Report dated May 30, 2016, in International Application PCT/US2016/019120.

Lutzky et al., "A Phase 1 study of MEDI4736, an anti-PD-L1 antibody, in patients with advanced solid tumors," Journal of Clinical Oncology; 2014 ASCO Annual Meeting, American Society of Clinical Oncology, vol. 32, No. 15 Suppl., p. 3001 (2014).

Segal et al., "Preliminary data from a multi-arm expansion study of MEDI4736, an anti-PD-L1 antibody," Journal of Clinical Oncology, vol. 32, No. 15 (Abstract) (2014).

Powles et al., "Inhibition of PD-L1 by MPDL3280A and clinical activity in pts with metastatic urothelial bladder cancer (UBC)," Journal of Clinical Oncology, 2014 ASCO Annual Meeting Abstracts, vol. 32, No. 15 (2014).

Ahmadzadeh, et al., Tumor antigen-specific CD8 T cells infiltrating the tumor express high levels of PD-1 and are functionally impaired, Blood, 114(8):1537-44 (2009).

Anonymous, "Avelumab in Metastatic or Locally Advanced Solid Tumors," (Javelin Solid Tumor)—Full Text View—ClinicalTrials. gov, Jan. 14, 2013, URL:https://clinicaltrials.gov/ct2/show/ NCT01772004?term=Avelumab&cond=HNSCC&rank=5 [retrieved on Jun. 23, 2017] the whole document (12 pages).

Anonymous, "Avelumab in Patients With Previously Treated Advanced Stage Classical Hodgkin's Lymphoma (Javelin Hodgkins)—Full Text View—ClinicalTrials.gov", Nov. 9, 2015 (Nov. 9, 2015), XP055384712, Retrieved from the Internet: URL:https://clinicaltrials. gov/ct2/show/NC T02603419?term=Avelumab&draw=1&rank=38 [retrieved on Jun. 23, 2017] the whole document (10 pages).

Anonymous, "Avelumab in Previously Untreated Patients With Epithelial Ovarian Cancer (Javelin Ovarian 100)—Full Text View— ClinicalTrials.gov", Mar. 12, 2016 (Mar. 15, 2016), XP055384715, Retrieved from the Internet: URL:https://clinicaltrials.gov/ct2/show/ NC T02718417?term=Avelumab&draw=1&rank=41 [retrieved on Jun. 23, 2017] the whole document (11 pages).

Anonymous, "History of Changes for Study: NCT02511184 Crizotinib Plus Pembrolizumab in ALK-Positive Advanced Non Small Cell Lung Cancer Patients," Clinical Trials.gov, Archive, Sep. 25, 2015 (11 pages).

Boyerinas, et al., "Antibody-Dependent Cellular Cytotoxicity Activity of a Novel Anti-PD-L1 Antibody Avelumab (MSB0010718C) on Human Tumor Cells," Cancer Immunology Research, 3(10):1148-1157 (2015).

Brown, et al., "Targeting DNA Repair in Cancer: Beyond PARP Inhibitors," Cancer Discovery 7(1):20-37 (2017).

Dong, et al., "B7-H1, a third member of the B7 family, co-stimulates T-cell proliferation and interleukin-10 secretion," Nature Medicine, 5(12):1365-9 (1999).

(56) References Cited

OTHER PUBLICATIONS

Fellouse, et al., "Synthetic antibodies from a four-amino-acid code: a dominant role for tyrosine in antigen recognition," PNAS, 101(34):12467-72 (2004).
Freeman, et al., "Engagement of the PD-1 immunoinhibitory receptor by a novel B7 family member leads to negative regulation of lymphocyte activation," Journal of Experimental Medicine, 192(7):1027-34 (2000).
Fury, et al., "Clinical Activity and Safety of Medi4736, an Anti-PD-L1 Antibody, In Patients With Head and Neck Cancer", Annals of Oncology, 25(Suppl 4)iv340-iv365 (2014).
Gadiot, et al., "Overall survival and PD-L1 expression in metastasized malignant melanoma," Cancer 117(10):2192-201 (2011).
Goytisolo, et al., "The absence of the DNA-dependent protein kinase catalytic subunit in mice results in anaphase bridges and in increased telomeric fusions with normal telomere length and G-strand overhang," Molecular and Cellular Biology, 21(11):3642-51 (2001).
Gulley, et al., "Exposure-response and PD-L1 expression analysis of second-line avelumab in patients with advanced NSCLC: Data from the Javelin Solid Tumor trial," Journal of Clinical Oncology, 35(15 Supp):9086 (2017)(2 pages).
Heery, et al., "Avelumab for metastatic or locally advanced previously treated solid tumours (Javelin Solid Tumor): a phase 1a, multicohort, dose-escalation trial," Lancet Oncology, 19(5):587-598 (2017).
Higuchi, et al., "CTLA-4 Blockade Synergizes Therapeutically with PARP Inhibition in BRCA1-Deficient Ovarian Cancer," Cancer Immunology Research, 3(11):1257-68 (2015).
Higuchi, et al., "PARP inhibition synergizes with anti-CTLA-4 immune therapy to promote rejection of peritoneal tumors in mouse models of ovarian cancer," Gynecologic Oncology, 133:115-116 (2014).
Horton et al., "Agonistic 4-1bb antibodies in combination with inhibitory antibodies against CTLA-4, PD-L1 or LAG-3 ACT or CD8+ T cells in the tumor microenvironment and synergize to promote regression of established tumors," Journal of Immunotherapy of Cancer, 2(Suppl 3):P213 (2014) (2 pages).
Iwai, et al., "Involvement of PD-L1 on tumor cells in the escape from host immune system and tumor immunotherapy by PD-L1 blockade," PNAS, 99(19):12293-7 (2002).
Keir, et al., "PD-1 and its ligands in tolerance and immunity," Annual Review of Immunology, 26:677-704 (2008).
Kelly, et al., "Avelumab (MSB00010718C; anti-PD-L1) in patients with advanced cancer: Safety data from 1300 patients enrolled in the phase 1b Javelin Solid Tumor Trial," Journal of Clinical Oncology, 343(15):3055 (4 pages) (2016).
Kohler, et al., "Continuous cultures of fused cells secreting antibody of predefined specificity," Nature, 256(5517):495-7 (1975).
Latchman, et al., "PD-L2 is a second ligand for PD-1 and inhibits T cell activation," Nature Immunology, 2(3):261-8 (2001).
Le, et al., Human antibodies for immunotherapy development generated via a human B cell hybridoma technology, PNAS,103(10):3557-62 (2006).
Le, et al., "PD-1 Blockade in Tumors with Mismatch-Repair Deficiency," New England Journal of Medicine, 372(26):2509-20 (2015).
Liao et al., "Treating patients with ALK-positive non-small cell lung cancer: latest evidence and management strategy," Therapeutics Advances in Medical Oncology, 7(5):274-290 (2015).
Morales-Kastresana et al., "Combined Immunostimulatory Monoclonal Antibodies Extend Survival in an Aggressive Transgenic Hepatocellular Carcinoma Mouse Model," Clinical Cancer Research; 19(22):6151-6162 (2013).
Okazaki, et al., "PD-1 and PD-1 ligands: from discovery to clinical application," International Immunology, 19(7):813-24 (2007).
Pal, et al., "Programmed death-1 inhibition in renal cell carcinoma: clinical insights and future directions," Clinical Advances in hematology and Oncology, 12(2):90-99 (2014).
Passiglia,et al., "PD-L1 expression as predictive biomarker in patients with NSCLC: a pooled analysis," Oncotarget, 7(15): 19738-19747 (2016).

Shitara, et al., "Phase I, open-label, multi-ascending dose trial of avelumab (MSB0010718C), an anti-PD-L1 monoclonal antibody, in Japanese patients with advanced solid tumors," Journal of Clinical Oncology, 22(15 Supp):3023 (2015) (2 pages).
Smith, et al., "The DNA-dependent protein kinase," Genes and Development, 13(8):916-34 (1999).
Taube, et al., "Colocalization of inflammatory response with B7-h1 expression in human melanocytic lesions supports an adaptive resistance mechanism of immune escape," Science Translational Medicine, 4(127):127ra37 (2012).
Thompson, et al., "Costimulatory B7-H1 in renal cell carcinoma patients: Indicator of tumor aggressiveness and potential therapeutic target," PNAS 101(49):17174-9 (2004).
Thompson, et al., "Tumor B7-H1 is associated with poor prognosis in renal cell carcinoma patients with long-term follow-up," Cancer Research, 66(7):3381-5 (2006).
Topalian, et al., "Safety, activity, and immune correlates of anti-PD-1 antibody in cancer," New England Journal of Medicine, 366 (26):2443 (2012).
Williams et al., "Telomere dysfunction and DNA-PKcs deficiency: characterization and consequence," Cancer Research, 69(5):2100-7 (2009).
Gross-Goupil, et al., "Axitinib: a review of its safety and efficacy in the treatment of adults with advanced renal cell carcinoma," Clinical Medicine Insights: Oncology, 7:269-277 (2013).
Amin, et al., "Nivolumab (anti-PD-1; BMS-936558, ONO-4538) in combination with sunitinib or pazopanib in patients (pts) with metastatic renal cell carcinoma (mRCC)," Journal of Clinical Oncology, 32(15):5010 (2014).
Heery, et al., "Phase I open-label, multiple ascending dose trial of MSB0010718C, an anti-PD-L1 monoclonal antibody, in advanced solid malignancies," Journal of Clinical Oncology, 32(15):3064 (2014).
Powles et al., "MPDL3280A (anti-PD-L1) Treatment Leads to Clinical Activity in Metastatic Bladder Cancer," Nature, 515(7528):558-562 (2014).
Tanaka et al., "Anti-PD-1 Antibody: Basics and Clinical Application," Japanese Journal of Cancer and Chemotherapy, 40(9):1145-1149 (2013).
Atkins et al., "Axitinib in Combination with Pembrolizumab in Patients with Advanced Renal Cell Carcinoma," presented at the European Society of Medical Oncology (ESM), Oct. 7 to 11, 2016, Copenhagen Denmark (1 page).
Atkins, et al., "Axitinib in Combination with Pembrolizumab in Patients with Advanced Renal Cell Cancer: a Non-Randomised, Open-Label, Dose-Finding, and Dose-Expansion Phase 1b Trial," The Lancel Oncology, 19(3):405-415 (2018).
Bai, et al., "A Guide to Rational Dosing of Monoclonal Antibodies," Clinical Pharmacokinetics, 51(2):119-135 (2012).
Bailey, et al., "Immune Checkpoint Inhibitors as Novel Targets for Renal Cell Carcinoma Therapeutics," The Cancer Journal, 19(4):348-352 (2013).
Choueiri, et al., "Trial in Progress: Phase 1b Dose-Finding Study of Axitinib Plus Pembrolizumab for First-Line Treatment of Advanced Renal Cell Carcinoma (RCC)," BJU International, 114(Supp. 4):4-5 (2014).
Clinical Trial NCT01472081, "Nivolumab (BMS-936558; MDX-1106) in Combination with Sunitinib, Pazopanib, or Ipilimumab in Subjects with Metastatic Renal Cell Carcinoma (RCC) (CheckMate 016)" (12 pages) (Study record version available online at clinicaltrials(dot)govict2/history/NCTO 1472081, submitted Jun. 12, 2019).
Clinical Trial NCT01472081, "Nivolumab (BMS-936558; MDX-1106) in Combination with Sunitinib, Pazopanib, or Ipilimumab in Subjects with Metastatic Renal Cell Carcinoma (RCC) (CheckMate 016)" (5 pages) (Study record version available online at clinicaltrials(dot)govict2/history/NCTO 1472081, submitted Jun. 12, 2019).
Clinical Trial NCT01984242, "A Study of Atezolizumab (an Engineered Anti-Programmed Death-Ligand 1 [PD-L1] Antibody) as Monotherapy or in Combination with Bevacizumab (Avastin®) Compared to Sunitinib (Sutent®) in Participants with Untreated Advanced Renal Cell Carcinoma (IMmotion150)" (5 pages) (Study record version available online at clinicaltrials(dot)govict2/history/NCT019 84242, submitted Jun. 12, 2019).

(56) References Cited

OTHER PUBLICATIONS

Clinical Trial NCT02036502, "A study of Pembrolizumab (MK-3475) in Combination with Standard of Care Treatments in Participants with Multiple Myeloma (MK-3475-023/Keynote-023)" (11 pages) (Study record version available online at ClinicalTrials(dot)gov archive, submitted Apr. 24, 2018).
Clinical Trial NCT02036502, "A study of Pembrolizumab (MK-3475) in Combination with Standard of Care Treatments in Participants with Multiple Myeloma (MK-3475-023/Keynote-023)" (5 pages) (Study record version available online at clinicaltrials(dot)gov/ct2/history/NCT02036502, submitted Apr. 24, 2018).
Clinical Trial NCT02039674, "A Study of Pembrolizumab (MK-3475) in Combination with Chemotherapy or Immunothempy in Participants with Non-Small Cell Lung Cancer (MK-3475-021/Keynote-021)" (5 pages) (Study record version available online at clinicaltrials(dot)govict2/history/NCT02039674, submitted Jun. 12, 2019).
Clinical Trial NCT02039674, "A Study of Pembrolizumab (MK-3475) in Combination with Chemotherapy or Immunothempy in Participants with Non-Small Cell Lung Cancer (MK-3475-021/Keynote-021)," (6 pages) (Study record version available online at clinicaltrials(dot)govict2/history/NCT02039674, submitted Jan. 11, 2019).
Clinical Trial NCT02133742, "A Dose Finding Study to Evaluate Safety, Drug Interaction, Tumor Markers of Axitinib in Combination with MK-3475 in Adult Patients with Previously Untreated Advanced Renal Cell Cancer" (1 page) (Study record version available online at clinicaltrials(dot)govict2/history/NCT02133742, submitted Jun. 20, 2019).
Clinical Trial NCT02133742, "A Dose Finding Study to Evaluate Safety, Drug Interaction, Tumor Markers of Axitinib in Combination with MK-3475 in Adult Patients with Previously Untreated Advanced Renal Cell Cancer" (8 pages) (Study record version available online at clinicaltrials(dot)govict2/history/NCT02133742, submitted Jun. 20, 2019).
Clinical Trial NCT02133742, "A Phase 1 B, Open Label, Dose Finding Study to Evaluate Safety, Pharmacokinetics and Pharmacodynamics Of Axitinib (AG-013736) In Combination With MK-3475 In Patients With Advanced Renal Cell Cancer," ClinicalTrials.gov archive, (May 7, 2014), Retrieved from the Internet: URL:https//clinicaltrials.govjarchive/NCT 02133742/2014 05 07 [retrieved on—Mar. 30, 2015] (3 pages).
Clinical Trial NCT02179918, "A Phase 1 Study of the 4-1B Agonsit PF-05082566 in Combination with the PD-1 Inhibitor MK-3475 in Patients with Advanced Solidy Tumors," Clinical Trials.gov (Jul. 1 2014), pp. 1-6. Retrieved from the Internet URL:https://clinicaltrials.gov/archive/NCT02179918/2014 07 01 (6 pages).
Clinical Trial NCT02331368, "Phase 2 Multi-Center Study of Anti-PD-1 during Lymphopenic State after HDT/ASCT for Multiple Myeloma" (4 pages) (Study record version available online at clinicaltrials(dot)govict2/history/NCT02331368, submitted Jul. 2, 2018).
Clinical Trial NTC02014636, "Safety and Efficacy Study of Pazopanib and MK 3475 in Advanced Renal Cell Carcinoma (RCC; Keynote-018)" (6 pages) (Study record version available online at https//clinicaltrials(dot)gov/ct2/history/NCT02014636, submitted Apr. 26, 2019).
Clinical Trials: NCT02014636, "A Phase I/II Study to Assess the Safety and Efficacy of Pazopanib and MK 34 75 in Subjects With Advanced Renal Cell Carcinoma," Clinical Trials.gov (Jan. 24, 2014), pp. 1-11. Retrieved from the Internet URL:https//clinicaltrials.gov/archive/NCT02014636/2014 01 24 [retrieved on Mar. 31, 2015] (11 pages).
Czarnecka, et al., "The Activity of Tyrosine Kinase Inhibitors on Clear Cell Renal Cell Carcinoma Tumor Initiating Cells in Hypoxic Microenvironment," BJUI Supplements, The 11th International Kidney Cancer Symposium Annual Meeting Proceedings, 110(Suppl. 2):1-20 (2012).

Dorff, et al., "Novel Tyrosine Kinase Inhibitors for Renal Cell Carcinoma," Expert Review of Clinical Pharmacology, 7(1):67-73 (2014).
Domblides, et al., "Emerging Antiangiogenics for Renal Cancer," Expert Opinion on Emerging Drugs, 18(4):495-511 (2013) (published online Dec. 2, 2013).
Dong et al., "Tumor-associated B7-H1 promotes T-cell apoptosis: a potential mechanism of immune evasion," Nature Medicine, 8(8):793-800 (2002).
Duraiswamy, et al., "Therapeutic PD-1 pathway blockade augments with other modalities of immunotherapy T-cell function to prevent immune decline in ovarian cancer," Cancer Research, 73(23):6900-6912 (2013).
Escudier, et al., "Axitinib for the management of metastatic renal cell carcinoma," Drugs in R&D 11(2):113-126 (2011).
Escudier, et al., "Optimal Management of Metastatic Renal Cell Carcinoma: Current Status," Drugs, 73:427-438 (2013).
European Search Report in European Application No. 18205542, dated Mar. 21, 2019 (8 pages).
FDA-Approved Patient Labeling for INLYTA, reference1D:3078397 (Jan. 2012) (22 pages).
Gao et al., "Overexpression of PD-L1 significantly associates with tumor aggressiveness and postoperative recurrence in human hepatocellular carcinoma," Clinical Cancer Research, 15(3):971-979 (2009).
Ghebeh et al., "FOXP3+ Tregs and B7-H1+/PD-1+ T lymphocytes co-infiltrate the tumor tissues of high-risk breast cancer patients: Implication for immunotherapy," BMC Cancer, 8:57 (12 pages) (2008).
Ghebeh et al., "The B7-H1 (PD-L1) T lymphocyte-inhibitory molecule is expressed in breast cancer patients with infiltrating ductal carcinoma: correlation with important high-risk prognostic factors," Neoplasia, 8(3):190-198 (2006).
Hamanishi et al., "Programmed cell death 1 ligand 1 and tumor-infiltrating CD8+ T lymphocytes are prognostic factors of human ovarian cancer," Proceeding of the National Academy of Sciences, 104(9):3360-3365 (2007).
Hamid et al., "Safety and tumor responses with lambrolizumab (anti-PD-1) in melanoma," New England Journal of Medicine, 369(2):134-144 (2013).
Hino et al., "Tumor cell expression of programmed cell death-1 ligand 1 is a prognostic factor for malignant melanoma," Cancer, 116(7):1757-1766 (2010).
Hu-Lowe et al., "Nonclinical antiangiogenesis and antitumor activities of axitinib (AG-013736), an oral, potent, and selective inhibitor of vascular endothelial growth factor receptor tyrosine kinases 1, 2, 3," Clinical Cancer Research, 14(22): 7272-7283 (2008).
Inman et al., "PD-L1 (B7-H1) expression by urothelial carcinoma of the bladder and BCG-induced granulomata: associations with localized stage progression," Cancer, 109(8):1499-1505 (2007).
Joshi, "ASCO GU 2018: Safety and Efficacy of Axitinib in Combination with Pembrolizumab in Patients with Advanced Renal Cell Cancer" available at www.urotoday.com (downloaded Oct. 19, 2018) (2 page).
Kaufman, et al., "The Society for Immunotherapy of Cancer Consensus Statement on Tumour Immunotherapy for the Treatment of Cutaneous Melanoma," Nature, 10:588-598 (2013).
Lipson, et al., "Durable Cancer Regression Off-Treatment and Effective Reinduction Therapy with an Anti-PD-1 Antibody," Clinical Cancer Research, 19:462-468 (2013).
Massari, et al., "PD-1 Blockade Therapy in Renal Cell Carcinoma: Current Studies and Future Promises," Cancer Treatment Reviews, 41:114-121 (2015).
McDermott et al., "PD-1 as a potential target in cancer therapy," Cancer Medicine, 2(5):662673 (2013).
Nakanishi et al., "Overexpression of B7-H1 (PD-L1) significantly associates with tumor grade and postoperative prognosis in human urothelial cancers," Cancer Immunology, Immunotherapy, 56(8):1173-1182 (2007).
Nomi et al., "Clinical significance and therapeutic potential of the programmed death-1 ligand/programmed death-1 pathway in human pancreatic cancer," Clinical Cancer Research, 13(7):2151-2157 (2007).

(56) References Cited

OTHER PUBLICATIONS

Ohigashi et al., "Clinical significance of programmed death-1 ligand-1 and programmed death-1 ligand-2 expression in human esophageal cancer," Clinical Cancer Research, 11(8):2947-2953 (2005).
Pal, et al., "Novel Therapies for Metastatic Renal Cell Carcinoma: Efforts to Expand beyond the VEGF/mTOR Signaling Paradigm," Molecular Cancer Therapeutics, 11(3):526-537 (2012).
Pardoll, "The Blockade of Immune Checkpoints in Cancer Immunotherapy," Nature, 12:252-264 (2016).
Patel, et al., "Clinical Cancer Advances 2013: Annual Report on Progress Against Cancer from the American Society of Clinical Oncology," Journal of Clinical Oncology, 32(2):129-160 (2014) (published online Dec. 10, 2013).
Patnaik et al., "Phase I Study of MK-3475 (Anti-PD-1 Monoclonal Antibody) in Patients with Advanced Solid Tumors," Journal of Clinical Oncology., 30(Supp.15):2512 (2012) (2 pages).
Patnaik et al., "Phase I Study of Pembrolizumab (MK-3475; Anti-PD-1 Monoclonal Antibody) in Patients with Advanced Solid Tumors," Clinical Cancer Research; 21(19) (2015).
PCT International Search Report, International Application No. PCT/US2015/014212, dated Apr. 10, 2015 (12 pages).
Procopio, et al., "Combination Therapies for Patients with Metastatic Renal Cell Carcinoma," Lancet, 19:281-283 (2018).
Rini, et al., "Five-Year Survival in Patients with Cytokine-Refractory Metastatic Renal Cell Carcinoma Treated with Axitinib," Clinical Genitourinary Cancer, 11(2):107-114 (2013).
Rini, et al., "Pembrolizumab Plus Axitinib Versus Sunitinib for Advanced Renal-Cell Carcinoma," The New England Journal of Medicine, 380:1116-1127 (2019).
Robert, et al., "Drug of the Year: Programmed Death-1 Receptor/Programmed Death-1 Ligand-1 Receptor Monoclonal Antibodies," European Journal of Cancer, 49:2968-2971 (2013).
Robert, et al., "LBA34-Pembrolizumab (Pembro:MK-3475) for Advanced Melanoma (MEL): Randomized Comparison of Two Dosing Schedules," Annals of Oncology, 25(Suppl.4):1-41 (Sep. 2014).
Rothermundt, et al., "Successful treatment with an anti-PD-1 antibody for progressing brain metastases in renal cell cancer," Annals of Oncology, 25:544-552 (2016).
Seliger, et al., "Abstracts from the 25th Annual Scientific Meeting of the International Society for Biological Therapy of Cancer (now the Society of Immunotherapy of Cancer)", Journal of Immunotherapy, 34(2):221-227 (2011).
Sequence Listing from International Application No. PCT/US2008/007463, filed Jun. 13, 2008 (24 pages).
Sharpe, et al., "The function of programmed cell death 1 and its ligands in regulating autoimmunity and infection," Nature Immunology, 8(3):239-245 (2007).
Shimauchi, et al., "Augmented expression of programmed death-1 in both neoplastic and non-neoplastic CD4+ T-cells in adult T-cell leukemia/lymphoma," International Journal of Cancer, 121(12):2585-2590 (2007).
Sliwkowski, et al., "Antibody Therapeutics in Cancer," Science, 341:1192-1198 (2013).
Solowiej, et al., "Characterizing the effects of the juxtamembrane domain on vascular endothelial growth factor receptor-2 enzymatic activity, autophosphorylation, and inhibition by axitinib," Biochemistry, 48(29):7019-31 (2009).
Stehle, et al., "Reduced Immunosuppressive Properties of Axitinib in Comparison with Other Tyrosine Kinase Inhibitors," J. Biol. Chem., 288(23):16334-16347 (2013).
Sznol, et al., "Phase 1b evaluation of MPDL3280A (anti-PDFL1) in connection with bevacizumab (bev) in patients (pts) with metastic renal cell carcinoma (mRCC)," Journal of Clinical Oncology, 33(7): Abstract (2015) (3 pages).
Taiwan Search Report for Application No. CN104103603, dated Sep. 11, 2018 (14 pages).
Tang, et al., "Programmed Death 1 Pathway Inhibition in Metastatic Renal Cell Cancer and Prostate Cancer," Current Oncology Reports, 15:98-104 (2013).
Thompson, et al., "PD-1 is expressed by tumor-infiltrating immune cells and is associated with poor outcome for patients with renal cell carcinoma," Clinical Cancer Research, 13(6):1757 1761 (2007).
Thompson, et al., "Significance of B7-H1 overexpression in kidney cancer," Clinical Genitourin Cancer, 5(3):206-211 (2006).
Tykodi, "Progress and Potential of Immune Checkpoint Blockage for Treating Advanced Renal Cell Carcinoma," Immunotherapy, 5(6):607-619 (2013).
Van Geel, et al., "Concise Drug Review: Pazopanib and Axitinib," The Oncologist, 17:1081-1089 (2012).
Wei, et al., "Combinatorial PD-1 blockade and CD137 activation has therapeutic efficacy in murine cancer models and synergizes with cisplatin," PLOS One, 8(12):e84927 (11 pages) (2013).
WHO Drug Information, vol. 27, No. 2, pp. 161-162 (2013).
Yang, et al., "PD-L1: PD-1 interaction contributes to the functional suppression of T-cell responses to human uveal melanoma cells in vitro," Investigative Ophthalmology & Visusal Science, 49(6):2518-2525 (2008.
Yasuda et al., "Simultaneous blockade of programmed death 1 and vascular endothelial growth factor receptor 2 (VEGFR2) induces synergistic anti-tumour effect in vivo," Clinical and Experimental Immunology, 172(3):500-506 (2013).
Yousaf, et al., "Axitinib in advanced renal-cell carcinoma," The Lancet Oncology, 12(13):1245-1246 (2013).

\* cited by examiner

Figure 1a

Heavy chain sequence of Avelumab - SEQ ID NO:7:

EVQLLESGGGLVQPGGSLRLSCAASGFTFS<u>SYIMM</u>WVRQAPGKGLEWVS<u>SIYPSG
GITFYADTVKG</u>RFTISRDNSKNTLYLQMNSLRAEDTAVYYCAR<u>IKLGTVTTVDY</u>WG
QGTLVTVSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKKVEPKSC
DKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPA
PIEKTISKAKGQPREPQVYTLPPSRDELTKNQVSLTCLVKGFYPSDIAVEWESNGQP
ENNYKTTPPVLDSDGSFFLYSKLTVDKSRWQQGNVFSCSVMHEALHNHYTQKSLS
LSPGK

Figure 1b

Heavy chain sequence of Avelumab, lacking the C-terminal K - SEQ ID NO:8:

EVQLLESGGGLVQPGGSLRLSCAASGFTFS<u>SYIMM</u>WVRQAPGKGLEWVS<u>SIYPSG
GITFYADTVKG</u>RFTISRDNSKNTLYLQMNSLRAEDTAVYYCAR<u>IKLGTVTTVDY</u>WG
QGTLVTVSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKKVEPKSC
DKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPA
PIEKTISKAKGQPREPQVYTLPPSRDELTKNQVSLTCLVKGFYPSDIAVEWESNGQP
ENNYKTTPPVLDSDGSFFLYSKLTVDKSRWQQGNVFSCSVMHEALHNHYTQKSLS
LSPG

Figure 2

Light chain sequence of Avelumab - SEQ ID NO:9:

QSALTQPASVSGSPGQSITISC<u>TGTSSDVGGYNYVS</u>WYQQHPGKAPKLMIY<u>DVSN
RPS</u>GVSNRFSGSKSGNTASLTISGLQAEDEADYYC<u>SSYTSSSTRV</u>FGTGTKVTVLG
QPKANPTVTLFPPSSEELQANKATLVCLISDFYPGAVTVAWKADGSPVKAGVETTK
PSKQSNNKYAASSYLSLTPEQWKSHRSYSCQVTHEGSTVEKTVAPTECS

SEQUENCE LISTING

<160> NUMBER OF SEQ ID NOS: 9

<210> SEQ ID NO 1
<211> LENGTH: 5
<212> TYPE: PRT
<213> ORGANISM: Artificial Sequence
<220> FEATURE:
<223> OTHER INFORMATION: from human Fab library

<400> SEQUENCE: 1

Ser Tyr Ile Met Met
1               5

<210> SEQ ID NO 2
<211> LENGTH: 17
<212> TYPE: PRT
<213> ORGANISM: Artificial Sequence
<220> FEATURE:
<223> OTHER INFORMATION: from human Fab library

<400> SEQUENCE: 2

Ser Ile Tyr Pro Ser Gly Gly Ile Thr Phe Tyr Ala Asp Thr Val Lys
1               5                   10                  15

Gly

<210> SEQ ID NO 3
<211> LENGTH: 11
<212> TYPE: PRT
<213> ORGANISM: Artificial Sequence
<220> FEATURE:
<223> OTHER INFORMATION: from human Fab library

<400> SEQUENCE: 3

Ile Lys Leu Gly Thr Val Thr Thr Val Asp Tyr
1               5                   10

<210> SEQ ID NO 4
<211> LENGTH: 14
<212> TYPE: PRT
<213> ORGANISM: Artificial Sequence
<220> FEATURE:
<223> OTHER INFORMATION: from human Fab library

<400> SEQUENCE: 4

Thr Gly Thr Ser Ser Asp Val Gly Gly Tyr Asn Tyr Val Ser
1               5                   10

<210> SEQ ID NO 5
<211> LENGTH: 7
<212> TYPE: PRT
<213> ORGANISM: Artificial Sequence
<220> FEATURE:
<223> OTHER INFORMATION: from human Fab library

<400> SEQUENCE: 5

Asp Val Ser Asn Arg Pro Ser
1               5

-continued

<210> SEQ ID NO 6
<211> LENGTH: 10
<212> TYPE: PRT
<213> ORGANISM: Artificial Sequence
<220> FEATURE:
<223> OTHER INFORMATION: from human Fab library

<400> SEQUENCE: 6

Ser Ser Tyr Thr Ser Ser Ser Thr Arg Val
1               5                   10

<210> SEQ ID NO 7
<211> LENGTH: 450
<212> TYPE: PRT
<213> ORGANISM: Artificial Sequence
<220> FEATURE:
<223> OTHER INFORMATION: from human Fab library

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 8
<211> LENGTH: 449
<212> TYPE: PRT
<213> ORGANISM: Artificial Sequence
<220> FEATURE:
<223> OTHER INFORMATION: from human Fab library

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

```
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
                275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Arg Asp Glu Leu Thr Lys Asn Gln Val Ser Leu
                355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
                435                 440                 445
Gly

<210> SEQ ID NO 9
<211> LENGTH: 216
<212> TYPE: PRT
<213> ORGANISM: Artificial Sequence
<220> FEATURE:
<223> OTHER INFORMATION: from human Fab library

<400> SEQUENCE: 9

Gln Ser Ala Leu Thr Gln Pro Ala Ser Val Ser Gly Ser Pro Gly Gln
1               5                   10                  15
Ser Ile Thr Ile Ser Cys Thr Gly Thr Ser Ser Asp Val Gly Gly Tyr
                20                  25                  30
Asn Tyr Val Ser Trp Tyr Gln Gln His Pro Gly Lys Ala Pro Lys Leu
                35                  40                  45
Met Ile Tyr Asp Val Ser Asn Arg Pro Ser Gly Val Ser Asn Arg Phe
            50                  55                  60
Ser Gly Ser Lys Ser Gly Asn Thr Ala Ser Leu Thr Ile Ser Gly Leu
65                  70                  75                  80
Gln Ala Glu Asp Glu Ala Asp Tyr Tyr Cys Ser Ser Tyr Thr Ser Ser
                85                  90                  95
Ser Thr Arg Val Phe Gly Thr Gly Thr Lys Val Thr Val Leu Gly Gln
                100                 105                 110
```

```
Pro Lys Ala Asn Pro Thr Val Thr Leu Phe Pro Pro Ser Ser Glu Glu
    115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
    195                 200                 205

Thr Val Ala Pro Thr Glu Cys Ser
    210                 215
```

PD-1/PD-L1 INHIBITORS FOR THE TREATMENT OF CANCER

CROSS-REFERENCE TO RELATED APPLICATIONS

This application is a U.S. National Stage Application filed under 35 U.S.C. § 371 of International Patent Application No. PCT/US2016/019120, filed Feb. 23, 2016, which claims priority to and the benefit of U.S. Provisional Patent Application No. 62/121,025, filed Feb. 26, 2015, U.S. Provisional Patent Application No. 62/133,721, filed Mar. 16, 2015, U.S. Provisional Patent Application No. 62/160,291, filed May 12, 2015, U.S. Provisional Patent Application No. 62/215,394, filed Sep. 8, 2015, and U.S. Provisional Patent Application No. 62/254,424, filed Nov. 12, 2015, the disclosures of each of which are incorporated herein by reference in their entireties.

The invention relates to methods of treating cancer in a subject, comprising administering to the subject a therapeutically effective amount of an inhibitor of the interaction between the PD-1 receptor and its ligand PD-L1.

BACKGROUND OF THE INVENTION

Cancer

Cancer is an abnormal growth of cells which tend to proliferate in an uncontrolled way and, in some cases, to metastasize (spread). Cancer is not one disease. It is a group of more than 100 different and distinctive diseases. Cancer can involve any tissue of the body and have many different forms in each body area. Most cancers are named for the type of cell or organ in which they start. If a cancer spreads (metastasizes), the new tumor bears the same name as the original (primary) tumor. The frequency of a particular cancer may depend on gender. While skin cancer is the most common type of malignancy for both men and women, the second most common type in men is prostate cancer and in women, breast cancer.

Lung Cancer

Lung cancer is the leading cause of cancer death in men and women in the USA and results in more cancer deaths than breast cancer, prostate cancer, and colorectal cancer combined. The American Cancer Society estimated that in 2014 there would be 224,210 new cases of lung cancer in the USA alone, and 159,260 people would die from their lung cancers (www.cancer.org: American Cancer Society Fact Sheet for 2014).

Worldwide, an estimated 1.8 million new cases of lung cancer were diagnosed in 2012, approximately 13% of the total of all new cancers diagnosed (Ferlay J, Soerjomataram I, Ervik M, et al. GLOBOCAN 2012 v1.0, Cancer Incidence and Mortality Worldwide: IARC Cancer Base No. 11 [Internet]. Lyon, France: International Agency for Research on Cancer; 2013).

Non-small cell lung cancer (NSCLC) accounts for approximately 80% of all cases of lung cancer. In NSCLC, results of standard therapy are poor except for the most localized cancers where surgery and/or combined modality therapy can provide a cure in a small percentage of patients.

In advanced-stage disease, chemotherapy offers modest benefit, though overall survival is poor (Chemotherapy for non-small cell lung cancer. Non-Small Cell Lung Cancer Collaborative Group. Cochrane Database Syst Rev (2): CD002139, 2000; Non-Small Cell Lung Cancer Collaborative Group. Chemotherapy in non-small cell lung cancer. BMJ 1995; 311(7010):899-909). There are 5 agents indicated for the treatment of advanced NSCLC in the second-line setting: docetaxel, pemetrexed, and the tyrosine kinase inhibitors (TKIs) erlotinib, gefitinib, and crizotinib. These agents have an overall response rate of <10% in an unselected patient population (Taxotere Prescribing Information. sanofi-aventis U.S. LLC; Alimta Prescribing Information. Eli Lilly and Company; Tarceva Prescribing Information. OSI Pharmaceuticals, Inc., and Genentech, Inc.; Iressa Prescribing Information. AstraZeneca Pharmaceuticals LP) and there is a growing body of evidence suggesting chemotherapy is preferable to erlotinib and gefitinib, especially in patients whose tumors do not harbor epidermal growth factor receptor (EGFR) activating mutations (Carnio S, Novelo S, Mele T, Levra M G, Scagliotti G V. Extending survival of Stage IV non-small cell lung cancer. Semin Oncol 2014; 41:69-92).

The programmed death 1 (PD-1) receptor and PD-1 ligands 1 and 2 (PD-L1, PD-L2) play integral roles in immune regulation. Expressed on activated T cells, PD-1 is activated by PD-L1 and PD-L2 expressed by stromal cells, tumor cells, or both, initiating T-cell death and localized immune suppression (Dong H, Zhu G, Tamada K, Chen L. B7-H1, a third member of the B7 family, co-stimulates T-cell proliferation and interleukin-10 secretion. Nat Med 1999; 5:1365-69; Freeman G J, Long A J, Iwai Y, et al. Engagement of the PD-1 immunoinhibitory receptor by a novel B7 family member leads to negative regulation of lymphocyte activation. J Exp Med 2000; 192:1027-34; Dong H, Strome S E, Salomao D R, et al. Tumor-associated B7-H1 promotes T-cell apoptosis: a potential mechanism of immune evasion. Nat Med 2002; 8:793-800. [Erratum, Nat Med 2002; 8:1039; Topalian S L, Drake C G, Pardoll D M. Targeting the PD-1/B7-H1(PD-L1) pathway to activate anti-tumor immunity. Curr Opin Immunol 2012; 24:207-12), potentially providing an immune-tolerant environment for tumor development and growth. Conversely, inhibition of this interaction can enhance local T-cell responses and mediate antitumor activity in nonclinical animal models (Dong H, Strome S E, Salomao D R, et al. Nat Med 2002; 8:793-800. [Erratum, Nat Med 2002; 8:1039; Iwai Y, Ishida M, Tanaka Y, et al. Involvement of PD-L1 on tumor cells in the escape from host immune system and tumor immunotherapy by PD-L1 blockade. Proc Natl Acad Sci USA 2002; 99:12293-97). In the clinical setting, treatment with antibodies that block the PD-1-PD-L1 interaction have been reported to produce objective response rates of 7% to 38% in patients with advanced or metastatic solid tumors, with tolerable safety profiles (Hamid O, Robert C, Daud A, et al. Safety and tumor responses with lambrolizumab (Anti-PD-1) in melanoma. N Engl J Med 2013; 369:134-44; Brahmer J R, Tykodi S S, Chow L Q, et al. Safety and activity of anti-PD-L1 antibody in patients with advanced cancer. N Engl J Med 2012; 366(26):2455-65; Topalian S L, Hodi F S, Brahmer J R, et al. Safety, activity, and immune correlates of anti-PD-1 antibody in cancer. N Engl J Med 2012; 366(26):2443-54; Herbst R S, Soria J-C, Kowanetz M, et al. Predictive correlates of response to the anti-PD-L1 antibody MPDL3280A in cancer patients. Nature 2014; 515:563-67). Notably, responses appeared prolonged, with durations of 1 year or more for the majority of patients.

There are relatively few studies looking at PD-L1 expression in NSCLC and estimates of the proportion of patients with PD-L1 positive (PD-L1+) tumors vary widely from 25% to close to 60% (Velcheti V, Schalper K A, Carvajal D E, et al. Programmed death ligand-1 expression in nonsmall cell lung cancer. Lab Invest 2014; 94:107-16; Chen Y B, Mu C Y, Huang J A. Clinical significance of programmed death-1 ligand-1 expression in patients with non-small cell lung cancer: a 5-year-follow-up study. Tumori 2012; 98(6): 751-55); however, treatment of unselected patient populations with NSCLC with antibodies directed against PD-1 or PD-L1 showed some clinical activity, with 30 responses recorded in 188 patients (Brahmer J R, Tykodi S S, Chow L Q, et al. N Engl J Med 2012; 366(26):2455-65; Topalian S L, Hodi F S, Brahmer J R, et al. N Engl J Med 2012; 366(26):2443-54; Herbst R S, Soria J-C, Kowanetz M, et al. Nature 2014; 515:563-67).

Merkel Cell Carcinoma

Merkel cell carcinoma is a rare and highly aggressive skin cancer, which, in most cases, is caused by the Merkel cell polyomavirus (MCV) discovered by scientists at the University of Pittsburgh in 2008. It is also known as cutaneous APUDoma, primary neuroendocrine carcinoma of the skin, primary small cell carcinoma of the skin, and trabecular carcinoma of the skin. Merkel cell carcinoma has suboptimal therapeutic options (Rabinowits G. Cancers 2014; 6:1180-94).

Approximately 80% of Merkel cell carcinomas are caused by MCV. The virus is clonally integrated into the cancerous Merkel cells. In addition, the virus has a particular mutation only when found in cancer cells, but not when it is detected in healthy skin cells. Direct evidence for this oncogenic mechanism comes from research showing that inhibition of production of MCV proteins causes MCV-infected Merkel carcinoma cells to die but has no effect on malignant Merkel cells that are not infected with this virus. MCV-uninfected tumors, which account for approximately 20% of Merkel cell carcinomas, appear to have a separate and as-yet unknown cause. No other cancers have been confirmed so far to be caused by this virus. This cancer is considered to be a form of neuroendocrine. While patients with a small tumor (less than 2 cm) that has not yet metastasized to regional lymph nodes have an expected 5-year survival rate of more than 80 percent, once a lesion has metastasized regionally, the rate drops to about 50 percent. Up to half of patients that have been seemingly treated successfully (i.e. that initially appear cancer-free) subsequently suffer a recurrence of their disease. Recent reviews cite an overall 5-year survival rate of about 60% for all MCC combined.

Gastric Cancer

Gastric cancer (GC) is the fifth most common malignancy, but ranks third as a cause of cancer deaths worldwide (Globocan Cancer Fact Sheet 2012). The highest regional rates of GC occur in Eastern and Southeastern Asia. In Japan, the age-standardized incidence rates are 45.7 and 16.5 for men and women, respectively. Histologically, GC consists of two major types (Lauren classification): intestinal and diffuse. Intestinal type tends to spread to both hematogenous and lymphatic route, whereas diffuse type tends to show peritoneal carcinomatosis or lymph node metastasis.

Platinum agent, cisplatin, or a fluoropyrimidine are predominantly included in chemotherapy regimens for the treatment of GC. Relative 5-year survival rates in the United States and China are 29% and 30%, respectively, but in Japan, a relative 5-year survival rate of 64% is achieved due to early diagnosis enabled by easy access to hospitals and clinics.

The observed 5-year overall survival (OS) for metastatic disease is dismal (approximately 4-5%).

Mesothelioma

Mesothelioma is an aggressive cancer of serosal surfaces such as pleura and peritoneum associated with a poor prognosis (Robinson B W, Lake R A., N Engl J Med 2005; 353: 1591-1603). Pleural mesothelioma often invades lungs and adjacent thoracic structures and presents with pleural effusions in a majority of patients, whereas peritoneal mesothelioma often presents with ascites. For patients with unresectable pleural mesothelioma chemotherapy using the regimen of cisplatin plus pemetrexed is the standard of care with a median overall survival of 1 year.

Urothelial Carcinoma

Transitional cell carcinoma (TOO, also urothelial cell carcinoma or UCC) is a type of cancer that typically occurs in the urinary system: the kidney, urinary bladder, and accessory organs. It is the most common type of bladder cancer and cancer of the ureter, urethra, and urachus. It is the second most common type of kidney cancer, but accounts for only five to 10 percent of all primary renal malignant tumors (en.wikipedia.org).

TCC arises from the transitional epithelium, a tissue lining the inner surface of these hollow organs. It can extend from the kidney collecting system to the bladder Transitional cell carcinoma (TOO) can be very difficult to treat. Treatment for localized stage TOO is surgical resection of the tumor, but recurrence is common. Some patients are given mitomycin (a chemotherapeutic drug) into the bladder either as a one-off dose in the immediate post operative period (within 24 hrs) or a few weeks after the surgery as a six dose regimen.

Ovarian Cancer

For women globally, ovarian cancer is the seventh most common cancer and the eighth leading cause of cancer death (Globocan Population Fact Sheet 2012). In the United States, the age-standardized incidence rate (ASR) based on 2007-2011 cases was 12.3 per 100,000 women, which represents an increase from an estimated ASR of 8.1 per 100,000 based on 2000-2009 cases. Because the disease lacks perceptible symptoms at an early stage, patients typically present with advanced disease.

The 5-year survival rate ranges from approximately 30% to 50% (SEER Stat Fact Sheet Ovary Cancer 2014). The addition of paclitaxel to platinum-based chemotherapy improved both progression-free survival (PFS) and overall survival (OS) in patients with advanced disease. Antiangiogenic agents, such as bevacizumab and pazopanib, have been shown to prolong PFS, but not OS. PARP inhibitors (eg, olaparib) added to chemotherapy have shown promise, but are predominately used in the maintenance setting. The majority of patients experience relapse, typically related to platinum resistance, thus making ovarian cancer an often fatal disease with few approved or effective treatment options (Luvero D, et al. Ther Adv Med Oncol. 2014; 6(5):229-239).

Breast Cancer

Breast cancer is the most common cancer in women both in the developed and less developed world. It is estimated that worldwide over 508 000 women died in 2011 due to breast cancer (Global Health Estimates, WHO 2013). Although breast cancer is thought to be a disease of the developed world, almost 50% of breast cancer cases and 58% of deaths occur in less developed countries (GLOBOCAN 2008).

The main treatments for breast cancer are: surgery, radiotherapy, chemotherapy, hormone therapy and biological therapy (targeted therapy).

In the treatment of local as well as metastatic breast cancer (MBC) anthracycline- or taxane-based chemotherapeutic regimens are used. More recently, these 2 agents have been combined together as first-line therapy for MBC. After the failure of anthracycline and taxane therapy, a patient with advanced or MBC has very few treatment options available. Chemotherapy with newer drugs like gemcitabine, capecitabine, and vinorelbine is being tested for effective palliation and longer survival.

Thymoma

Thymoma (thymic epithelial tumors, TETs) is a tumor originating from the epithelial cells of the thymus. Thymoma is an uncommon tumor, best known for its association with the neuromuscular disorder myasthenia gravis; thymoma is found in 20% of patients with myasthenia gravis.

Adrenocortical Carcinoma

Adrenocortical carcinoma, also adrenal cortical carcinoma (ACC) and adrenal cortex cancer, is an aggressive cancer originating in the cortex (steroid hormone-producing tissue) of the adrenal gland. Adrenocortical carcinoma is a rare tumor, with incidence of 1-2 per million population annually. Adrenocortical carcinoma has a bimodal distribution by age, with cases clustering in children under 5, and in adults 30-40 years old.

BRIEF DESCRIPTION OF THE FIGURES

FIG. 1a (SEQ ID NO:7) shows the full length heavy chain sequence of Avelumab.

FIG. 1b (SEQ ID NO:8) shows the heavy chain sequence of Avelumab without the C-terminal lysine.

FIG. 2 (SEQ ID NO:9) shows the light chain sequence of Avelumab.

GENERAL DESCRIPTION OF THE INVENTION

It is therefore an aspect of the present invention to provide a method of treating cancer in a subject, comprising administering to the subject a therapeutically effective amount of an inhibitor of the interaction between the PD-1 receptor and its ligand PD-L1.

Specific types of cancer to be treated according to the invention include, but are not limited to, lung cancer, bladder cancer, squamous cell carcinoma of the head and neck, renal cell carcinoma, gastric cancer, Merkel cell carcinoma, gastric/gastroesophageal junction cancer, breast cancer, colorectal cancer, castration-resistant prostate cancer, melanoma, ovarian cancer, adrenocortical carcinoma, mesothelioma, esophageal squamous cell carcinoma (ESCC), thymoma, adrenocortical carcinoma and urothelial carcinoma, which cancers may be untreated or previously treated, primary or metastatic, refractory, or recurrent.

In one embodiment of the invention the subject is human, the PD-1 receptor is human PD-1 receptor, and PD-L1 is human PD-L1.

In a preferred embodiment of the invention the inhibitor binds to PD-L1.

In a more preferred embodiment the inhibitor is an anti-PD-L1 antibody. In some embodiments, the anti-PD-L1 antibody comprises three complementarity determining regions (CDRs) (SEQ ID NOs: 1, 2 and 3) from the heavy chain amino acid sequence shown in FIGS. 1a (SEQ ID NO:7) and 1b (SEQ ID NO:8), and three CDRs (SEQ ID NOs: 4, 5 and 6) from the light chain amino acid sequence shown in FIG. 2 (SEQ ID NO:9), as marked by underlining, and described in further detail in WO2013079174. In a more preferred embodiment, the anti-PD-L1 antibody is Avelumab, having the heavy and light chain sequences shown in FIG. 1a or 1b and 2 (SEQ ID NOs: 7 or 8, and 9).

FIG. 1a (SEQ ID NO:7) shows the full length heavy chain sequence of Avelumab. It is frequently observed, however, that in the course of antibody production the C-terminal lysine (K) of the heavy chain is cleaved off. This modification has no influence on the antibody-antigen binding. Therefore, in some embodiments the C-terminal lysine (K) of the heavy chain sequence of Avelumab is absent. The heavy chain sequence of Avelumab without the C-terminal lysine is shown in FIG. 1b (SEQ ID NO:8).

In another embodiment of the invention the anti-PD-L1 antibody is administered at a dose of 10 mg/kg body weight every other week (i.e. every two weeks, or "Q2W")).

In one embodiment, the method results in an objective response, preferably a complete response or partial response in the subject.

In one embodiment, the inhibitor is administered intravenously (e.g. as an intravenous infusion). Preferably, the inhibitor is administered as a one hour intravenous infusion.

In one aspect, the cancer is identified as a PD-L1 positive cancer.

In one aspect, the cancer is locally advanced unresectable, metastatic, or recurrent cancer.

In one embodiment, the locally advanced unresectable, metastatic, or recurrent non-small cell lung cancer has progressed after chemotherapy, wherein the chemotherapy preferably comprises a platinum containing chemotherapeutic agent, more preferably the chemotherapy is platinum-containing doublet chemotherapy.

In a further aspect the cancer to be treated is non-small cell lung cancer.

In one embodiment, the subject having non-small cell lung cancer has previously received chemotherapy. In a preferred embodiment, the chemotherapy comprises a platinum containing chemotherapeutic agent. In more preferred embodiment the chemotherapy is platinum-containing doublet chemotherapy.

In another embodiment the non-small cell lung cancer has progressed after chemotherapy. In a preferred embodiment the chemotherapy comprises a platinum containing chemotherapeutic agent. In more preferred embodiment the chemotherapy is platinum-containing doublet chemotherapy.

In a further aspect the cancer to be treated is Merkel cell carcinoma, which is metastatic and/or has progressed after chemotherapy.

In yet another particular aspect the cancer to be treated is mesothelioma, which is advanced and unresectable.

In yet another aspect the cancer to be treated is ovarian cancer, which is heavily pretreated, recurrent or refractory.

In yet another particular aspect the cancer to be treated is gastric or gastroesophageal junction cancer which has progressed after chemotherapy.

In yet another particular aspect the cancer to be treated is urothelial carcinoma which is locally advanced or metastatic.

In yet another particular aspect the cancer to be treated is breast cancer. In yet another particular aspect the cancer to be treated is breast cancer which is locally advanced or metastatic.

Also provided is the use of an anti-PD-L1 antibody in the manufacture of a medicament for the treatment of cancer in an individual. Also provided is an anti-PD-L1 antibody for use in the treatment of cancer.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact polyclonal or monoclonal antibodies, but also, unless otherwise specified, any antigen binding fragment thereof that competes with the intact antibody for specific binding, fusion proteins comprising an antigen binding portion (e.g., antibody-drug conjugates), any other modified configuration of the immunoglobulin molecule that comprises an antigen recognition site, antibody compositions with polyepitopic specificity, multispecific antibodies (e.g., bispecific antibodies).

Antigen binding fragments include, for example, Fab, Fab', F(ab')2, Fd, Fv, domain antibodies (dAbs, e.g., shark and camelid antibodies), fragments including complementarity determining regions (CDRs), single chain variable fragment antibodies (scFv), maxibodies, minibodies, intrabodies, diabodies, triabodies, tetrabodies, v-NAR and bis-scFv, and polypeptides that contain at least a portion of an immunoglobulin that is sufficient to confer specific antigen binding to the polypeptide.

The term "immunoglobulin" (Ig) is used interchangeably with "antibody" herein. The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain at its other end. The $V_L$ is aligned with the $V_H$ and the CL is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see e.g., Basic and Clinical Immunology, 8th Edition, Daniel P. Sties, Abba I. Terr and Tristram G. Parsolw (eds), Appleton & Lange, Norwalk, Conn., 1994, page 71 and Chapter 6. The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG and IgM, having heavy chains designated α, δ, ε, γ and μ, respectively. The γ and α classes are further divided into subclasses on the basis of relatively minor differences in the $C_H$ sequence and function, e.g., humans express the following subclasses: IgG1, IgG2A, IgG2B, IgG3, IgG4, IgA1 and IgK1.

An "isolated" antibody is one that has been identified, separated and/or recovered from a component of its production environment (E.g., natural or recombinant). Preferably, the isolated polypeptide is free of association with all other components from its production environment. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (1) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant cells since at least one component of the antibody's natural environment will not be present. Ordinarily, however, an isolated polypeptide or antibody will be prepared by at least one purification step.

The "variable region" or "variable domain" of an antibody refers to the amino-terminal domains of the heavy or light chain of the antibody. The variable domains of the heavy chain and light chain may be referred to as "VH" and "VL", respectively. These domains are generally the most variable parts of the antibody (relative to other antibodies of the same class) and contain the antigen binding sites.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen binding site of antibodies (see Kabat et al, Sequences of Immunological Interest, Fifth Edition, National Institute of Health, Bethesda, Md. (1991)). The constant domains are not involved directly in the binding of antibody to an antigen, but exhibit various effector functions, such as participation of the antibody in antibody-dependent cellular toxicity.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein., Nature, 256:495-97 (1975); Hongo et al, Hybridoma, 14 (3): 253-260 (1995), Harlow et al, Antibodies: A Laboratory Manual, (Cold Spring Harbor Laboratory Press, $2^{nd}$ ed. 1988); Hammerling et al, in: Monoclonal Antibodies and T-Cell Hybridomas 563-681 (Elsevier, N.Y., 1981)), recombinant DNA methods (see, e.g., U.S. Pat. No. 4,816,567), phage-display technologies (see, e.g., Clackson et al, Nature, 352: 624-628 (1991); Marks et al, J. Mol Biol. 222: 581-597 (1992); Sidhu et al, J. Mol Biol. 338(2): 299-310 (2004); Lee et al, J. Mol Biol. 340(5): 1073-1093 (2004); Fellouse, Proc. Natl. Acad. ScL USA 101(34): 12467-12472 (2004); and Lee et al, J. Immunol. Methods 284(1-2): 119-132 (2004), and technologies for producing human or humanlike antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al, Proc. Natl. Acad. ScL USA 90: 2551 (1993); Jakobovits et al, Nature 362: 255-258 (1993); Bruggemann et al, Year in Immunol. 7:33 (1993); U.S. Pat. Nos. 5,545,807; 5,545,806; 5,569,825; 5,625,126; 5,633,425; and 5,661,016; Marks et al, Bio/Technology 10: 779-783 (1992); Lonberg et al, Nature 368: 856-859 (1994); Morrison, Nature 368: 812-813 (1994); Fishwild et al, Nature Biotechnol 14: 845-851 (1996); Neuberger, Nature Biotechnol. 14: 826 (1996); and Lonberg and Huszar, Intern. Rev. Immunol. 13: 65-93 (1995).

An "antigen binding fragment" of an antibody, or "antibody fragment" comprises a portion of an intact antibody, which is still capable of antigen binding and/or the variable region of the intact antibody. Examples of antibody fragments include Fab, Fab', F(ab')2 and Fv fragments; diabodies; linear antibodies (see U.S. Pat. No. 5,641,870, Example 2; Zapata et al, Protein Eng. 8H0): 1057-1062 [1995]); single-chain antibody molecules and multispecific antibodies formed from antibody fragments. Papain digestion of antibodies produced two identical antigen-binding fragments, called "Fab" fragments, and a residual "Fe" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site. "Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of the sFv, see Pluckthun in The Pharmacology of Monoclonal Antibodies, vol. 113, Rosenburg and Moore eds., Springer-Verlag, New York, pp. 269-315 (1994). "Functional fragments" of the antibodies of the invention comprise a portion of an intact antibody, generally including the antigen binding or variable region of the intact antibody or the Fc region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al, Proc. Natl. Acad. ScL USA 90: 6444-6448 (1993).

The term "nanobodies" refers to single-domain antibodies which are fragments consisting of a single monomeric variable antibody domain. Like a whole antibody, they are able to bind selectively to a specific antigen. With a molecular weight of only 12-15 kDa, single-domain antibodies are much smaller than common antibodies (150-160 kDa). The first single-domain antibodies were engineered from heavy-chain antibodies found in camelids. Gibbs, W. Wayt (August 2005). "Nanobodies". Scientific American Magazine.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al, Proc. Natl. Acad. ScL USA, 81:6851-6855 (1984)). As used herein, "humanized antibody" is used a subset of "chimeric antibodies."

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from an HVR (hereinafter defined) of the recipient are replaced by residues from an HVR of a non-human species (donor antibody) such as mouse, rat, rabbit or non-human primate having the desired specificity, affinity, and/or capacity. In some instances, framework ("FR") residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. The number of these amino acid substitutions in the FR are typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al, Nature 321:522-525 (1986); Riechmann et al, Nature 332:323-329 (1988); and Presta, Curr. Op. Struct. Biol. 2:593-596 (1992). See also, for example, Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409.

A "human antibody" is an antibody that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, J. Mol. Biol, 227: 381 (1991); Marks et al, J. Mol. Biol, 222:581 (1991). Also available for the preparation of human monoclonal antibodies are methods described in Cole et al, Monoclonal Antibodies and Cancer Therapy, Alan R. Liss, p. 77 (1985); Boerner et al, J. Immunol, 147(I):86-95 (1991). See also van Dijk and van de Winkel, Curr. Opin. Pharmacol, 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al, Proc. Natl. Acad. Sci. USA, 103:3557-3562 (2006) regarding human antibodies generated via a human B-cell hybridoma technology.

Avelumab (formerly designated MSB0010718C) is a fully human monoclonal antibody of the immunoglobulin (Ig) G1 isotype. Avelumab selectively binds to PD-L1 and competitively blocks its interaction with PD-1.

Compared with anti-PD-1 antibodies that target T-cells, Avelumab targets tumor cells, and therefore is expected to have fewer side effects, including a lower risk of autoimmune-related safety issues, as blockade of PD-L1 leaves the PD-L2-PD-1 pathway intact to promote peripheral self-tolerance (Latchman Y, Wood C R, Chernova T, et al. PD-L1 is a second ligand for PD-1 and inhibits T cell activation. Nat Immunol 2001; 2(3):261-68).

Avelumab, its sequence and many of its properties have been described in WO2013079174, where it is designated A09-246-2, having the heavy chain and light sequences according to SEQ ID NOs: 32 and 33, as shown in FIG. 1 (SEQ ID NO:7) and FIG. 2 (SEQ ID NO:9), of this patent application. As shown in WO2013079174, one of Avelumab's properties is its ability to exert antibody-dependent cell-mediated cytotoxicity (ADCC), thereby directly acting on PD-L1 bearing tumor cells by inducing their lysis without showing any significant toxicity.

Typically, the inhibitors, e.g. antibodies or antibody fragments according to the invention are incorporated into pharmaceutical compositions suitable for administration to a subject, wherein the pharmaceutical composition comprises the inhibitors, e.g. antibodies or antibody fragments and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof.

In many cases, it is preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the inhibitors, e.g. antibodies or antibody fragments.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans. The preferred mode of administration is parenteral (e. g., intravenous, subcutaneous, intraperitoneal, intramuscular). In a preferred embodiment, the inhibitor, e.g. antibody or antibody fragment is administered by intravenous infusion or injection. In another preferred embodiment, the inhibitor, e.g. antibody or antibody fragment is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i. e., inhibitor, e.g. antibody or antibody fragment) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

A "therapeutically effective amount" of an inhibitor, e.g. antibody or antibody fragment of the invention refers to an amount effective, at dosages and for periods of time necessary, to achieve the desired therapeutic result. Such therapeutically effective amount may vary according to factors such as the disease state, age, sex, and weight of the individual, and the ability of the inhibitor, e.g. antibody or antibody fragment to elicit a desired response in the individual. A therapeutically effective amount is also one in which any toxic or detrimental effects of the inhibitor, e.g. antibody or antibody fragment are outweighed by the therapeutically beneficial effects.

"Chemotherapy" is a therapy involving a "chemotherapeutic agent", which is a chemical compound useful in the treatment of cancer. Examples of chemotherapeutic agents include alkylating agents such as thiotepa and cyclophosphamide; alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol); beta-lapachone; lapachol; colchicines; betulinic acid; a camptothecin (including the synthetic analogue topotecan (CPT-11 (irinotecan), acetylcamptothecin, scopolectin, and 9-aminocamptothecin); bryostatin; pemetrexed; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; TLK-286; CDP323, an oral alpha-4 integrin inhibitor; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e. g., calicheamicin, especially calicheamicin gammaII and calicheamicin omegaII (see, e.g., Nicolaou et ah, Angew. Chem Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, doxorubicin HCl liposome injection and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine, tegafur, capecitabine, an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, and imatinib (a 2-phenylaminopyrimidine derivative), as well as other c-Kit inhibitors; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); thiotepa; taxoids, e.g., paclitaxel, albumin-engineered nanoparticle formulation of paclitaxel, and doxetaxel; chloranbucil; 6-thioguanine; mercaptopurine; methotrexate; platinum analogs such as cisplatin and carboplatin; vinblastine; platinum; etoposide (VP-16); ifosfamide; mitoxantrone; vincristine; oxaliplatin; leucovovin; vinorelbine; novantrone; edatrexate; daunomycin; aminopterin; ibandronate; topoisomerase inhibitor RFS 2000; difluorometlhylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin combined with 5-FU and leucovovin.

"Platinum-based chemotherapy" as used herein refers to therapy with one or more platinum-based chemotherapeutic agents, optionally in combination with one or more other chemotherapeutic agents.

"Platinum-containing doublet chemotherapy" as used herein is a combination therapy consisting of a platinum containing chemotherapeutic, such as cisplatin or carboplatin, and a second chemotherapeutic, such as gemcitabine, vinorelbine, irinotecan, paclitaxel or docetaxel.

"Pemetrexed based chemotherapy" as used herein refers to therapy with one or more Pemetrexed-based chemotherapeutic agents, optionally in combination with one or more other chemotherapeutic agents.

The phrase "progressed after chemotherapy" refers to progression of the carcinoma while receiving chemotherapy (i.e. refractory) or progression of the carcinoma within 12 months (e.g. within 6 months) after completing the chemotherapy regimen.

"Objective response" refers to a measurable response, including complete response (CR) or partial response (PR).

"Complete response" or "complete remission" refers to the disappearance of all signs of cancer in response to treatment. This does not always mean the cancer has been cured.

"Partial response" refers to a decrease in the size of one or more tumors or lesions, or in the extent of cancer in the body, in response to treatment.

A "PD-L1 positive" cancer is one comprising cells which have PD-L1 present at their cell surface. Preferably, the cancer is "PD-L1 positive" according to the invention, when between at least 0.1% and at least 10% of the cells of the cancer have PD-L1 present at their cell surface. More preferably, the cancer is "PD-L1 positive", when between at least 0.5% and 5% of the cells of the cancer have PD-L1 present at their cell surface. Most preferably, the cancer is "PD-L1 positive", when at least 1% of the cells of the cancer have PD-L1 present at their cell surface.

The term "PD-L1 positive" also refers to a cancer that produces sufficient levels of PD-L1 at the surface of cells thereof, such that an anti-PD-L1 inhibitor (e.g. antibody) has a therapeutic effect, mediated by the binding of the said anti-PD-L1 inhibitor (e.g. antibody) to PD-L1.

In a preferred embodiment the PD-L1 expression is determined by immunohistochemistry (IHC).

A subject with non-small cell lung cancer that has "progressed after chemotherapy" includes a subject whose non-small cell lung cancer has progressed while receiving chemotherapy, or whose non-small cell lung cancer has progressed after completing a chemotherapy regimen, e.g. within 12 months (or 6 months) of completing chemotherapy.

"Advanced" cancer is one which has spread outside the site or organ of origin, either by local invasion or metastasis. Accordingly, the term "advanced" cancer includes both locally advanced and metastatic disease.

"Recurrent" cancer is one which has regrown, either at the initial site or at a distant site, after a response to initial therapy, such as surgery. A "locally recurrent" cancer is cancer that returns after treatment in the same place as a previously treated cancer.

"Unresectable" cancer is not able to be removed (resected) by surgery.

"Metastatic" cancer refers to cancer which has spread from one part of the body (e.g. the lung) to another part of the body.

"Locally advanced" cancer refers to cancer that has spread to nearby tissues or lymph nodes, but not metastasized.

"Advanced unresectable" cancer is one which has spread outside the site or organ of origin, either by local invasion or metastasis and which is not able to be removed (resected) by surgery.

"Subject" includes a human patient. The patient may be a "cancer patient," i.e. one who is suffering or at risk for suffering from one or more symptoms of cancer, in particular non-small cell lung cancer.

"Infusion" or "infusing" refers to the introduction of a drug-containing solution into the body through a vein for therapeutic purposes. Generally, this is achieved via an intravenous (IV) bag.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

"Antibody-dependent cell-mediated cytotoxicity" or ADCC refers to a form of cytotoxicity in which secreted Ig bound onto Fc receptors (FcRs) present on certain cytotoxic cells (e.g., natural killer (NK) cells, neutrophils and macrophages) enable these cytotoxic effector cells to bind specifically to an antigen-bearing target cell and subsequently kill the target cell with cytotoxins. The antibodies "arm" the cytotoxic cells and are required for killing of the target cell by this mechanism. The primary cells for mediating ADCC, NK cells, express FcγRIII only, whereas monocytes express FcγRI, FcγRII and FcγRIII. Fc expression on hematopoietic cells is summarized in Table 3 on page 464 of Ravetch and Kinet, Annu. Rev. Immunol. 9: 457-92 (1991).

Specific Description of the Invention

Non-Small Cell Lung Cancer

In one specific aspect the invention provides a method of treating non-small cell lung cancer in a subject, comprising administering to the subject a therapeutically effective amount of an inhibitor of the interaction between the PD-1 receptor and its ligand PD-L1.

In one embodiment of this aspect the subject in which non-small cell lung cancer is treated is human, the PD-1 receptor is human PD-1 receptor, and PD-L1 is human PD-L1.

In one embodiment the inhibitor binds to PD-L1. Preferably, the inhibitor is an anti-PD-L1 antibody, or an antigen binding fragment thereof. More preferably, the anti-PD-L1 antibody, or an antigen binding fragment thereof, comprises in its heavy chain the three complementarity determining regions (CDR's) according to SEQ ID NOs: 1, 2 and 3, and in its light chain the three complementarity determining regions (CDR's) according to SEQ ID NOs: 4, 5 and 6. Most preferably the anti-PD-L1 antibody is Avelumab, having the heavy and light chain sequences shown in FIG. 1a or 1b and 2 (SEQ ID NOs: 7 or 8 and 9), or an antigen binding fragment thereof.

In one embodiment the non-small cell lung cancer is a squamous cell carcinoma. Alternatively, the non-small cell lung cancer is a non-squamous cell carcinoma.

In one embodiment the non-small cell lung cancer is recurrent non-small cell lung cancer. Alternatively or additionally the non-small cell lung cancer is stage IV non-small cell lung cancer.

NSCLC's are staged according to stages I-IV, with I being an early stage and IV being the most advanced. The treatment of NSCLC depends on the staging of the cancer. As used herein the phrase "stage IV non-small cell lung cancer" refers to a non-small cell lung cancer having one or more of the following characteristics: i) there are one or more tumors in both lungs; cancer is found in fluid around the lungs or the heart; and/or iii) cancer has spread to other parts of the body, such as the brain, liver, adrenal glands, kidney, or bone. Additionally, the tumor may be any size and cancer may have spread to lymph nodes.

In one embodiment the subject has not previously received therapy for metastatic or recurrent disease. Alternatively or additionally the subject has not previously received a diagnosis for an autoimmune disease. Alternatively or additionally the subject has not previously received treatment with an immune checkpoint therapy.

As used herein the phrase "autoimmune disease" refers to diseases, or disorder having an autoimmune component, including, but not limited to rheumatoid arthritis, multiple sclerosis, systemic lupus erythromatosis (SLE), sclerodema, diabetes, inflammatory bowel disease, psoriasis and atherosclerosis.

As used herein, the phrase "immune checkpoint therapy" refers to therapy with one or more agents capable of altering the function of immune checkpoints, including the CTLA-4, LAG-3, B7-H3, B7-H4, Tim3, BTLA, KIR, A2aR, CD200 and/or PD-1 pathways. Exemplary immune checkpoint modulating agents include anti-CTLA-4 antibody (e.g., ipilimumab), anti-LAG-3 antibody, anti-B7-H3 antibody, anti-B7-H4 antibody, anti-Tim3 antibody, anti-BTLA antibody, anti-KIR antibody, anti-A2aR antibody, anti CD200 antibody, anti-PD-1 antibody, anti-PD-L1 antibody, anti-CD28 antibody, anti-CD80 or -CD86 antibody, anti-B7RP1 antibody, anti-B7-H3 antibody, anti-HVEM antibody, anti-CD137 or -CD137L antibody, anti-OX40 or -OX40L antibody, anti-CD40 or -CD40L antibody, anti-GAL9 antibody, anti-IL-10 antibody and A2aR drug.

In one embodiment the non-small cell lung cancer is identified as a PD-L1 positive cancer. Alternatively or additionally the non-small cell lung cancer is identified as negative for an activating EGFR mutation. Alternatively or additionally the non-small cell lung cancer is identified as negative for an ALK rearrangement.

The presence or absence of an activating mutation can be determined in a patient sample. In this regard the EGFR status of NSCLC can be readily determined using assays well known in the art. It has been shown that EGF receptor (EGFR) is overexpressed in certain types of cancers of the lung (adenocarcinomas, including bronchoalveolar carcinoma (BAC) and non-small cell lung cancer (NSCLC)). The amplification and/or overexpression of the EGF receptors on the membranes of tumor cells is associated with a poor prognosis.

As used herein the term "ALK rearrangement" refers to any rearrangement or fusion of the anaplastic lymphoma kinase (ALK).gene. In this regard the ALK gene status of NSCLC can be readily determined using techniques well known in the art (e.g. FISH and PCR analysis).

In one embodiment the inhibitor is an anti-PD-L1 antibody, which is administered at a dose of approximately 10 mg/kg body weight every other week.

In one embodiment the anti-PD-L1 antibody is administered as an intravenous infusion. Preferably the antibody is administered as a one hour intravenous infusion.

In one embodiment the method results in an objective response, preferably a complete response or a partial response.

Urothelial Carcinoma

In one specific aspect the invention provides a method of treating urothelial carcinoma in a subject, comprising administering to the subject a therapeutically effective amount of an inhibitor of the interaction between the PD-1 receptor and its ligand PD-L1.

In one embodiment of this aspect the subject in which urothelial carcinoma is treated is human, the PD-1 receptor is human PD-1 receptor, and PD-L1 is human PD-L1.

In one embodiment the inhibitor binds to PD-L1. Preferably, the inhibitor is an anti-PD-L1 antibody, or an antigen binding fragment thereof. More preferably, the anti-PD-L1 antibody, or an antigen binding fragment thereof, comprises In its heavy chain the three complementarity determining regions (CDR's) according to SEQ ID NO's 1, 2 and 3, and in its light chain the three complementarity determining regions (CDR's) according to SEQ ID NO's 4, 5 and 6. Most preferably the anti-PD-L1 antibody is Avelumab, having the heavy and light chain sequences shown in FIGS. 1a or 1b and 2 (SEQ ID NO's 7 or 8 and 9), or an antigen binding fragment thereof.

In one embodiment the urothelial carcinoma is locally advanced or metastatic.

In one embodiment the carcinoma is a urinary bladder carcinoma, a urethral carcinoma, a renal pelvis carcinoma, or a ureter carcinoma.

In one embodiment the subject has previously received chemotherapy.

In one embodiment the urothelial carcinoma has progressed after chemotherapy.

In one embodiment the locally advanced or metastatic urothelial cancer has not progressed during or following completion of firstline chemotherapy.

In one embodiment the urothelial carcinoma is identified as a PD-L1 positive cancer.

In one embodiment the inhibitor is an anti-PD-L1 antibody, which is administered at a dose of approximately 10 mg/kg body weight every other week.

In one embodiment the anti-PD-L1 antibody is administered as an intravenous infusion.

In one embodiment the anti-PD-L1 antibody is administered as a one hour intravenous infusion.

In one embodiment the method results in an objective response, preferably a complete response or a partial response.

Mesothelioma

In one specific aspect the invention provides a method of treating mesothelioma in a subject, comprising administering to the subject a therapeutically effective amount of an inhibitor of the interaction between the PD-1 receptor and its ligand PD-L1.

In one embodiment of this aspect the subject in which mesothelioma is treated is human, the PD-1 receptor is human PD-1 receptor, and PD-L1 is human PD-L1.

In one embodiment the inhibitor binds to PD-L1. Preferably, the inhibitor is an anti-PD-L1 antibody, or an antigen binding fragment thereof. More preferably, the anti-PD-L1 antibody, or an antigen binding fragment thereof, comprises In its heavy chain the three complementarity determining regions (CDR's) according to SEQ ID NOs: 1, 2 and 3, and in its light chain the three complementarity determining regions (CDR's) according to SEQ ID NOs: 4, 5 and 6. Most preferably the anti-PD-L1 antibody is Avelumab, having the heavy and light chain sequences shown in FIGS. 1a or 1b and 2 (SEQ ID NOs: 7 or 8 and 9), or an antigen binding fragment thereof.

In one embodiment the subject has previously received chemotherapy. In one embodiment the chemotherapy comprises a platinum based chemotherapy. In one embodiment the chemotherapy comprises a pemetrexed based chemotherapy.

In one embodiment the chemotherapy comprises a platinum based chemotherapy and comprises a pemetrexed based chemotherapy. For example the chemotherapy regimen may comprise a combined platinum-pemetrexed regimen. Alternatively, the chemotherapy regimen may comprise sequential administration of a platinum based chemotherapy and pemetrexed based chemotherapy, for example administration of a platinum based chemotherapy and subsequent administration of a pemetrexed based chemotherapy.

In one embodiment the mesothelioma has progressed after chemotherapy.

In one embodiment the mesothelioma is a pleural mesothelioma. In one embodiment the mesothelioma is a peritoneal mesothelioma.

In one embodiment the mesothelioma is advanced unresectable mesothelioma.

In one embodiment the mesothelioma is identified as a PD-L1 positive cancer.

In one embodiment the inhibitor is an anti-PD-L1 antibody, which is administered at a dose of approximately 10 mg/kg body weight every other week.

In one embodiment the anti-PD-L1 antibody is administered as an intravenous infusion.

In one embodiment the anti-PD-L1 antibody is administered as a one hour intravenous infusion.

In one embodiment the method results in an objective response, preferably a complete response or a partial response.

Merkel Cell Carcinoma

In one specific aspect the invention provides a method of treating Merkel cell carcinoma in a subject, comprising administering to the subject a therapeutically effective amount of an inhibitor of the interaction between the PD-1 receptor and its ligand PD-L1.

In one embodiment of this aspect the subject in which Merkel cell carcinoma is treated is human, the PD-1 receptor is human PD-1 receptor, and PD-L1 is human PD-L1.

In one embodiment the inhibitor binds to PD-L1. Preferably, the inhibitor is an anti-PD-L1 antibody, or an antigen binding fragment thereof. More preferably, the anti-PD-L1 antibody, or an antigen binding fragment thereof, comprises In its heavy chain the three complementarity determining regions (CDR's) according to SEQ ID NOs: 1, 2 and 3, and in its light chain the three complementarity determining regions (CDR's) according to SEQ ID NOs: 4, 5 and 6. Most preferably the anti-PD-L1 antibody is Avelumab, having the heavy and light chain sequences shown in FIGS. 1a or 1b and 2 (SEQ ID NOs: 7 or 8 and 9), or an antigen binding fragment thereof.

In one embodiment the subject has previously received chemotherapy.

In one embodiment the Merkel cell carcinoma has progressed after chemotherapy.

In one embodiment the Merkel cell carcinoma is identified as a PD-L1 positive cancer.

In one embodiment the Merkel cell carcinoma is metastatic.

In one embodiment the inhibitor is an anti-PD-L1 antibody, which is administered at a dose of approximately 10 mg/kg body weight every other week.

In one embodiment the anti-PD-L1 antibody is administered as an intravenous infusion.

In one embodiment the anti-PD-L1 antibody is administered as a one hour intravenous infusion.

In one embodiment the method results in an objective response, preferably a complete response or a partial response.

Gastric or Gastroesophageal Junction Cancer

In one aspect the invention provides a method of treating gastric or gastroesophageal junction cancer in a subject, comprising administering to the subject a therapeutically effective amount of an inhibitor of the interaction between the PD-1 receptor and its ligand PD-L1.

In one embodiment of this aspect of the invention the subject in which gastric or gastroesophageal junction cancer is treated is human, the PD-1 receptor is human PD-1 receptor, and PD-L1 is human PD-L1.

In one embodiment the inhibitor binds to PD-L1. Preferably, the inhibitor is an anti-PD-L1 antibody, or an antigen binding fragment thereof. More preferably, the anti-PD-L1 antibody, or an antigen binding fragment thereof, comprises In its heavy chain the three complementarity determining regions (CDR's) according to SEQ ID NOs: 1, 2 and 3, and in its light chain the three complementarity determining regions (CDRs) according to SEQ ID NOs: 4, 5 and 6. Most preferably, the anti-PD-L1 antibody is Avelumab, having the heavy and light chain sequences shown in FIGS. 1a or 1b and 2 (SEQ ID NOs: 7 or 8 and 9), or an antigen binding fragment thereof.

In one embodiment the subject has previously received chemotherapy.

In one embodiment the gastric or gastroesophageal junction cancer has progressed after chemotherapy. Alternatively, the gastric or gastroesophageal junction cancer has not progressed after chemotherapy and the inhibitor is administered as a maintenance therapy, preferably as a switch maintenance therapy.

Where the subject has previously received chemotherapy and the gastric or gastroesophageal junction cancer has not progressed after chemotherapy the inhibitor may be administered as a maintenance therapy. As used herein the phrase "maintenance therapy" refers to therapy received after a first-line regimen, wherein the subject has either stable or responding cancerous disease (i.e. non-progressors). Maintenance therapy can be either "switch maintenance" where the maintenance entails switching to a maintenance therapy that was not a compenent of the regimen used in the first line setting, or "continuous maintenance" where the maintenance wntails the continuation of a therapy that was used in the first line setting.

In one embodiment the gastric or gastroesophageal junction cancer is identified as a PD-L1 positive cancer.

In one embodiment the gastric or gastroesophageal junction cancer is locally advanced unresectable or metastatic gastric or gastroesophageal junction cancer.

In one embodiment the cancer treatment is a third-line treatment of unresectable, recurrent, or metastatic gastric or gastroesophageal junction adenocarcinoma.

In one embodiment the inhibitor is an anti-PD-L1 antibody, which is administered at a dose of approximately 10 mg/kg body weight every other week.

In one embodiment the anti-PD-L1 antibody is administered as an intravenous infusion.

In one embodiment the anti-PD-L1 antibody is administered as a one hour intravenous infusion.

In one embodiment the method results in an objective response, preferably a complete response or a partial response.

Ovarian Cancer

In one aspect the invention provides a method of treating ovarian cancer in a subject, comprising administering to the subject a therapeutically effective amount of an inhibitor of the interaction between the PD-1 receptor and its ligand PD-L1.

In one embodiment of this aspect the subject in which ovarian cancer is treated is human, the PD-1 receptor is human PD-1 receptor, and PD-L1 is human PD-L1.

In one embodiment the inhibitor binds to PD-L1. Preferably, the inhibitor is an anti-PD-L1 antibody, or an antigen binding fragment thereof. More preferably, the anti-PD-L1 antibody, or an antigen binding fragment thereof, comprises In its heavy chain the three complementarity determining regions (CDR's) according to SEQ ID NO's 1, 2 and 3, and in its light chain the three complementarity determining regions (CDRs) according to SEQ ID NOs: 4, 5 and 6. Most preferably the anti-PD-L1 antibody is Avelumab, having the heavy and light chain sequences shown in FIGS. 1a or 1b and 2 (SEQ ID NOs: 7 or 8 and 9), or an antigen binding fragment thereof.

In one embodiment the subject has previously received chemotherapy.

In one embodiment the subject has previously been heavily pre-treated.

As used herein the phrase "heavily pre-treated" refers to a patient having received three or more prior therapies. More particularly the phrase "heavily pre-treated" refers to patients six or more courses of chemotherapy containing platinum or an alkylating agent, or at least two courses of nitrosourea or mitomycin.

In one embodiment the ovarian cancer has progressed after chemotherapy. In one embodiment the ovarian cancer is stage III-IV cancer.

In one embodiment the ovarian cancer is recurrent or refractory ovarian cancer.

In one embodiment the ovarian cancer is recurrent or refractory ovarian cancer stage III-IV cancer.

Ovarian cancers are staged according to stages I-IV, with I being an early stage and IV being the most advanced. The treatment of ovarian cancer depends on the staging of the cancer. As used herein the phrase "stage III ovarian cancer" refers to an ovarian cancer in which the cancer is in one or both ovaries or fallopian tubes, and one or both of the following are present: i) the cancer has spread beyond the pelvis to the lining of the abdomen and/or ii) the cancer has spread to lymph nodes in the back of the abdomen (retroperitoneal lymph nodes). As used herein the phrase "stage IV ovarian cancer" refers to an ovarian cancer in which the cancer has spread to the inside of the spleen, liver, lungs, or other organs located outside the peritoneal cavity.

In one embodiment the inhibitor is an anti-PD-L1 antibody, which is administered at a dose of approximately 10 mg/kg body weight every other week.

In one embodiment the inhibitor is an anti-PD-L1 antibody the anti-PD-L1 antibody is administered as an intravenous infusion.

In one embodiment the anti-PD-L1 antibody is administered as a one hour intravenous infusion.

In one embodiment the method results in an objective response, preferably a complete response or a partial response.

Breast Cancer

In one aspect the invention provides a method of treating breast cancer in a subject, comprising administering to the subject a therapeutically effective amount of an inhibitor of the interaction between the PD-1 receptor and its ligand PD-L1.

In one embodiment of this aspect the subject in which breast cancer is treated is human, the PD-1 receptor is human PD-1 receptor, and PD-L1 is human PD-L1.

In one embodiment the inhibitor binds to PD-L1. Preferably, the inhibitor is an anti-PD-L1 antibody, or an antigen binding fragment thereof. More preferably, the anti-PD-L1 antibody, or an antigen binding fragment thereof, comprises In its heavy chain the three complementarity determining regions (CDRs) according to SEQ ID NOs: 1, 2 and 3, and in its light chain the three complementarity determining regions (CDRs) according to SEQ ID NOs: 4, 5 and 6. Most preferably the anti-PD-L1 antibody is Avelumab, having the heavy and light chain sequences shown in FIGS. 1a or 1b and 2 (SEQ ID NOs: 7 or 8 and 9), or an antigen binding fragment thereof.

In one embodiment the subject has previously received chemotherapy. In a preferred embodiment the said chemotherapy comprises the use of taxane and/or anthracycline.

In one embodiment the breast cancer locally advanced or metastatic.

In one embodiment the breast cancer has progressed after chemotherapy.

In one embodiment the ovarian cancer is recurrent or refractory breast cancer.

In one embodiment the inhibitor is an anti-PD-L1 antibody, which is administered at a dose of approximately 10 mg/kg body weight every other week.

In one embodiment the inhibitor is an anti-PD-L1 antibody the anti-PD-L1 antibody is administered as an intravenous infusion.

In one embodiment the anti-PD-L1 antibody is administered as a one hour intravenous infusion.

In one embodiment the method results in an objective response, preferably a complete response or a partial response.

Thymoma

In one aspect the invention provides a method of treating thymoma in a subject, comprising administering to the subject a therapeutically effective amount of an inhibitor of the interaction between the PD-1 receptor and its ligand PD-L1.

In one embodiment of this aspect the subject in which thymoma is treated is human, the PD-1 receptor is human PD-1 receptor, and PD-L1 is human PD-L1.

In one embodiment the inhibitor binds to PD-L1. Preferably, the inhibitor is an anti-PD-L1 antibody, or an antigen binding fragment thereof. More preferably, the anti-PD-L1 antibody, or an antigen binding fragment thereof, comprises In its heavy chain the three complementarity determining regions (CDRs) according to SEQ ID NOs: 1, 2 and 3, and in its light chain the three complementarity determining regions (CDRs) according to SEQ ID NOs: 4, 5 and 6. Most preferably the anti-PD-L1 antibody is Avelumab, having the heavy and light chain sequences shown in FIGS. 1a or 1b and 2 (SEQ ID NOs: 7 or 8 and 9), or an antigen binding fragment thereof.

In one embodiment the subject has previously received chemotherapy and/or radiotherapy. In a preferred embodiment the subject has previously received chemotherapy. In another preferred embodiment the subject has previously received radiotherapy. In a third preferred embodiment the subject has previously received chemotherapy and radiotherapy.

In one embodiment the inhibitor is an anti-PD-L1 antibody, which is administered at a dose of approximately 10 mg/kg body weight every other week.

In one embodiment the inhibitor is an anti-PD-L1 antibody the anti-PD-L1 antibody is administered as an intravenous infusion.

In one embodiment the anti-PD-L1 antibody is administered as a one hour intravenous infusion.

In one embodiment the method results in an objective response, preferably a complete response or a partial response.

Adrenocortical Carcinoma

In one aspect the invention provides a method of treating adrenocortical carcinoma in a subject, comprising administering to the subject a therapeutically effective amount of an inhibitor of the interaction between the PD-1 receptor and its ligand PD-L1.

In one embodiment of this aspect the subject in which adrenocortical carcinoma is treated is human, the PD-1 receptor is human PD-1 receptor, and PD-L1 is human PD-L1.

In one embodiment the inhibitor binds to PD-L1. Preferably, the inhibitor is an anti-PD-L1 antibody, or an antigen binding fragment thereof. More preferably, the anti-PD-L1 antibody, or an antigen binding fragment thereof, comprises In its heavy chain the three complementarity determining regions (CDRs) according to SEQ ID NOs: 1, 2 and 3, and in its light chain the three complementarity determining regions (CDRs) according to SEQ ID NOs: 4, 5 and 6. Most preferably the anti-PD-L1 antibody is Avelumab, having the heavy and light chain sequences shown in FIGS. 1a or 1b and 2 (SEQ ID NOs: 7 or 8 and 9), or an antigen binding fragment thereof.

In one embodiment the subject has previously received chemotherapy. In a preferred embodiment the said chemotherapy is platinum-based.

In one embodiment the adrenocortical carcinoma locally advanced or metastatic.

In one embodiment the adrenocortical carcinoma has progressed after chemotherapy.

In one embodiment the adrenocortical carcinoma is recurrent or refractory adrenocortical carcinoma.

In one embodiment the inhibitor is an anti-PD-L1 antibody, which is administered at a dose of approximately 10 mg/kg body weight every other week.

In one embodiment the inhibitor is an anti-PD-L1 antibody the anti-PD-L1 antibody is administered as an intravenous infusion.

In one embodiment the anti-PD-L1 antibody is administered as a one hour intravenous infusion.

In one embodiment the method results in an objective response, preferably a complete response or a partial response.

ABBREVIATIONS

AE Adverse event
AUC Area Under Curve
Av Avelumab
BOR Best overall response
CR Complete response
CTCAE Common Terminology Criteria for Adverse Events
ECOG Eastern Cooperative Oncology Group
EGFR Epidermal growth factor receptor
EORTC European Organization for Research and Treatment of Cancer
EQ-5D EuroQOL 5-dimensions questionnaire
IERC Independent Endpoint Review Committee
IHC Immunohistochemistry
IV Intravenous
ITT Intention To Treat
LA Locally Advanced
NSCLC Non-small cell lung cancer
ORR Objective response rate
OS Overall survival
PD Progressive Disease
PFS Progression-free survival
PR Partial response
QLQ-LC13 Quality of Life Questionnaire-Lung Cancer
RECIST 1.1 Revised Guidelines for Response Evaluation Criteria in Solid Tumors
SAE Serious adverse event
SD Stable Disease
SOC Standard Of Care
TEAE Treatment-Emergent Adverse Event

EXAMPLE 1

This example is about a phase Ib trial testing Avelumab in patients with metastatic or recurrent non-small-cell lung cancer progressing after platinum-based chemotherapy.

Patients were treated with Avelumab at 10 mg/kg Q2W until confirmed progression, unacceptable toxicity, or any criterion for withdrawal occurred. Tumors were assessed every 6 weeks (RECIST 1.1). Unconfirmed best overall response (BOR), progression-free survival (PFS), and overall survival (OS) were evaluated. Subgroup analyses based on histology and tumor PD-L1 expression at baseline as assessed by immunohistochemistry were performed.

184 patients with metastatic or recurrent NSCLC progressing after platinum-based doublet chemotherapy were treated with Avelumab at 10 mg/kg as a 1-h infusion Q2W and had ≥6 months follow-up. Median treatment duration was 12.2 weeks (range 2-64). Median age was 65y (range 31-83) and ECOG performance status was 0 [29.9%], 1 [69.6%], or >1 [0.5%]. Histology was adenocarcinoma (62%), squamous cell carcinoma (29%), or other (9%). Tumors were PD-L1+ in 86% of evaluable patients (n=142; 1% tumor expression cutoff). Treatment-related treatment-emergent AEs (TEAEs; all grades) occurring >10% were fatigue (25.0%), infusion-related reaction (IRR; 20.7%), and nausea (13.0%). Treatment-related grade ≥3 TEAEs occurred in 23 patients (12.5%), including 4 grade 3/4 IRRs and 2 grade 5 events (radiation pneumonitis, acute respiratory failure). Objective responses were observed in 25 (13.6%) patients (95% CI: 9.0, 19.4), with 1 CR and 24 PRs—in these patients tumor shrinkage by >30% was observed; 19 responses were ongoing at data cutoff. Responses were reported in all histologies: adenocarcinoma (13 patients; ORR, 11.4% [95% CI: 6.2, 18.7]), squamous cell (7 patients; 13.2% [5.5, 25.3]), and other (5 patients; 29.4% [10.3, 56.0]). Stable disease was observed in 68 patients (37.0%). Median PFS was 11.6 weeks (95% CI: 8.4, 13.7) and the 1-year PFS rate was 18.1% (95% CI: 12.0, 25.2). Median OS was 8.4 months. The ORR in PD-L1+ patients (n=122) was 15.6% (95% CI: 9.6, 23.2) and 10.0% (95% CI: 1.2, 31.7) in PD-L1− patients (n=20). Median PFS in PD-L1+ patients was 12.0 weeks vs 5.9 weeks in PD-L1− patients. Median OS for the PD-L1+ population was 8.6 months (95% CI: 8.1, not estimable) and 4.9 months (95% CI: 2.76, not estimable) for PD-L1− patients.

Conclusions:

Avelumab showed a manageable safety profile and preliminary clinical activity in patients with advanced NSCLC independent of tumor histology. Tumor expression of PD-L1 was associated with a higher RR and longer median PFS compared with PD-L1− tumors (using the 1% tumor expression cutoff).

EXAMPLE 2

This example is about a multicenter, international, randomized, open-label, Phase III trial of Avelumab versus Docetaxel in subjects with locally advanced unresectable, metastatic, or recurrent NSCLC that has progressed after a platinum doublet. In the trial approximately 650 subjects, among them 522 PD-L1 assay positive subjects, are randomized in a 1:1 ratio to receive either Avelumab at a dose of 10 mg/kg once every 2 weeks, or docetaxel at a starting dose of 75 mg/m$^2$ once every 3 weeks. Subjects are stratified according to PD-L1 assay status (positive versus negative expression in tumor cells) and NSCLC histology and EGFR status (squamous cell versus non-squamous cell EGFR normal versus non-squamous cell EGFR-activating mutations).

Subjects return to the clinic at regular intervals for assessments. Tumor measurements by computed tomography (CT) scan or magnetic resonance imaging (MRI) are performed every 6 weeks to determine response to treatment. A central imaging laboratory is used to read and interpret all CT/MRI data. Response is evaluated using the RECIST 1.1 and as adjudicated by a blinded IERC. Treatment continues until disease progression, significant clinical deterioration (clinical progression), unacceptable toxicity, or any criterion for withdrawal from the trial or trial drug is fulfilled.

Subjects receiving Avelumab who have experienced a CR are treated for a minimum of 6 months and a maximum of 12 months after confirmation, at the discretion of the Investigator.

Subjects assigned to docetaxel are treated until disease progression, unacceptable toxicity, or any of the criteria for withdrawal from trial treatment is fulfilled.

Subjects attend clinic visits at regular intervals to receive trial treatment and for efficacy and safety assessments.

The primary endpoint for the trial is OS time, defined as the time from randomization to death.

Secondary endpoints include PFS time according to RECIST 1.1 and as adjudicated by the IERC, BOR according to RECIST 1.1 and as adjudicated by the IERC, changes in subject-reported outcomes/quality of life as assessed by the EQ-5D, the EORTC QLQ-C30, and module QLQ-LC13 questionnaires, and safety and tolerability of the trial drugs as measured by the incidence of AEs, SAEs, deaths, and laboratory abnormalities.

Exploratory endpoints include the duration of response according to RECIST 1.1 and as adjudicated by the IERC, tumor shrinkage in target lesions per time point from Baseline, serum titers of anti-Avelumab antibodies and neutralizing effects of anti-drug antibodies, PK profile of Avelumab; exposure-safety and exposure-efficacy relationships will be determined, relationship between PD-L1 expression levels in tumor cells and cells of the tumor microenvironment (for example, infiltrating lymphocytes) and OS, PFS, and ORR, changes in soluble factors (for example, cytokine profiles), and changes in gene expression (gene expression profiling).

Avelumab is a sterile, clear, and colorless solution intended for i.v. administration. It is presented at a concentration of 20 mg/mL in single-use glass vials closed with a rubber stopper and sealed with an aluminum polypropylene flip-off seal. Docetaxel is a white to almost-white powder. Docetaxel is supplied commercially (Hospira, Lake Forest, Ill.) as 20 mg/$^2$ mL and 160/16 mL in polysorbate 80/dehydrated alcohol suspension.

In this trial, the treatment is given until PD, significant clinical deterioration (clinical progression), unacceptable toxicity, or any criterion for withdrawal from the trial or trial drug is fulfilled.

EXAMPLE 3

This example is about a multicenter, international, single-arm, open-label, phase II trial to evaluate the efficacy and safety of Avelumab in patients with metastatic Merkel cell carcinoma who have received one or more prior lines of chemotherapy.

Up to 84 eligible subjects will receive Avelumab at a dose of 10 mg/kg as a 1 h intravenous infusion one every 2 weeks. Treatment will continue until disease progression, unacceptable toxicity, or if any criterion for withdrawal occurs.

The primary objective of the trial is to assess the clinical activity of Avelumab as determined by the objective response rate according to RECIST 1.1 by an Independent Endpoint Review Committee. Tumor measurements to determine response will be performed every 6 weeks. Secondary objectives include assessment of the duration of response, progression-free survival time, overall survival, and safety. Exploratory objectives include assessment of immune-related responses and evaluation of PD-L1 expression and its potential association with the response.

EXAMPLE 4A

This example is about a trial enrolling patients with histologically confirmed stage IV (according to IASLC) or recurrent NSCLC who have not previously received treatment for metastatic or recurrent disease. In addition, this cohort is restricted to patients without an activating EGFR mutation or ALK rearrangement. Patients with unknown EGFR or ALK status will be tested during screening and are required to have negative status for inclusion. Eligible patients also must have tumor archival material or fresh biopsy, an ECOG performance status of 0 or 1 at the time of trial entry, and disease with at least 1 measurable lesion according to RECIST 1.1.

Exclusion criteria include prior therapy with immune checkpoint drugs or a known history of autoimmune disease.

Up to 150 eligible patients will receive Avelumab at 10 mg/kg as an infusion Q2W. Treatment will continue until disease progression, unacceptable toxicity, or any criterion for withdrawal occurs. Treatment may be continued despite progression according to RECIST 1.1 if the patient clinical status is stable and according to investigator opinion there is no need to start salvage therapy. The primary objective of the trial is to assess the safety and tolerability of Avelumab as a first-line therapy. Select secondary objectives include: assessment of best overall response (BOR) and progression-free survival (PFS) according to RECIST 1.1; assessment of immune-related BOR and immune-related PFS (using modified Immune-Related Response Criteria); and assessment of overall survival. Association between tumor PD-L1 expression and efficacy will be evaluated. Immunomonitoring of cellular and soluble markers and intratumoral cellular surveillance will also be carried out. At each visit during the treatment phase, adverse events will be assessed and graded according to NCI-CTCAE v4.0. Tumor evaluation will be performed every 6 weeks until progression.

EXAMPLE 4B

This example is about a multicenter, international, randomized, open-label, Phase III trial in chemotherapy naïve (first line) metastatic or recurrent, PD-L1 positive NSCLC subjects comparing Avelumab to first line platinum-based chemotherapy. The trial will be conducted at approximately 243 sites globally in North America, South America, Asia, Africa, and Europe.

It consists of a 28-day screening period, followed by the treatment phase (4 days after randomization). Visits will take place every 2 weeks (−3/+1 days) for subjects assigned to Avelumab and every 3 weeks (−3/+1 days) for subjects assigned to receive chemotherapy.

Approximately 570 subjects will be screened, of which 420, will be randomized in a 1:1 ratio to receive either:

Avelumab at a dose of 10 mg/kg as a 1-hour intravenous (IV) infusion once every 2 weeks until disease progression or unacceptable toxicities, or Investigator's choice platinum containing chemotherapy regimen to be administered in 3-week cycles up to a maximum of 6 cycles of IV injection until disease progression or unacceptable toxicities consisting of one of the following:

for patients whose tumor is of non-squamous histology: pemetrexed (500 mg/m$^2$) in combination with cisplatin (75 mg/m$^2$ administered on Day 1 of each cycle) or carboplatin (AUC 6 mg/mL*min administered on Day 1 of each cycle).

for patients whose tumor is of squamous histology:
paclitaxel (200 mg/m2) plus carboplatin (AUC 6 mg/mL*min administered on Day 1 of each cycle); or
gemcitabine (1250 mg/m$^2$ administered on Day 1 and Day 8) plus cisplatin (75 mg/m$^2$) or
gemcitabine (1000 mg/m$^2$ administered on Day 1 and Day 8) plus carboplatin (AUC 5 mg/mL*min)

Subjects will be stratified according to NSCLC histology (squamous versus non-squamous cell). Tumor measurements by computed tomography (CT) scan or magnetic resonance imaging (MRI) will be performed every 6 weeks to determine response to treatment. Response will be evaluated using the Response Evaluation Criteria in Solid Tumors version 1.1 (RECIST 1.1).

Treatment with Avelumab will continue until disease progression or unacceptable toxicity. Treatment with chemotherapy will continue until disease progression or unacceptable toxicity or after the completion of 6 cycles of chemotherapy. Patients with non-squamous histology are authorized to continue to receive pemetrexed as a maintenance therapy even if they have not completed the 6 cycles of combination therapy, platinum salt and pemetrexed.

Patients assigned to platinum-based chemotherapy will have the option to receive Avelumab (10 mg/kg every 2 weeks until disease progression or unacceptable toxicity) only after disease progression has been confirmed by the Independent radiologist.

Decisions regarding medical management of subjects will be made by the Investigator; however, the secondary endpoint determinations (response and progressive disease [PD]) will be according to the central imaging assessment and review by a blinded Independent Review Committee (IRC).

Adverse events (AEs) will be assessed throughout the trial and evaluated using the National Cancer Institute (NCI) Common Technology Criteria version for Adverse Events version 4.03 (CTCAE v 4.03).

Periodic evaluations of the trial data will be conducted by an Independent Data Monitoring Committee (IDMC) to ensure subject safety, and the validity and scientific merit of the trial.

Discontinuation Visit:

All subjects who discontinue trial treatment for an AE should have a full safety evaluation at the time of discontinuation (Discontinuation visit).

Follow-Up Phase:

The Follow-up Phase starts when the decision has been made to stop trial drug treatment. Subjects will have:
an End-of-Treatment visit at 28 days (±5 days) after the last administration of trial treatment or before the start of any other antineoplastic therapy, and
a Safety Follow-up visit 12 weeks (±2 weeks) after the last administration of trial treatment.

Planned Number of Subjects:

Approximately 570 subjects will be screened. Accrual will proceed up to a target number of 420 subjects enrolled.

Primary Endpoints:

The primary endpoint for the trial is the PFS, defined as the time from date of randomization until date of the first documentation of PD as determined by the independent response committee/radiologist (per RECIST 1.1) or death due to any cause in the absence of documented PD, whichever occurs first.

Secondary Endpoints:
The secondary endpoints include:
PFS time in PD L1++ subjects,
BOR according to RECIST 1.1 and as adjudicated by the IRC,
OS time (defined as the time from randomization to the date of death),
changes in subject-reported outcomes/quality of life (as-sessed by the EQ-5D, and the EORTC QLQ-C30, and module QLQ-LC13 questionnaires)
safety endpoints (including AEs, clinical laboratory assessments, vital signs, physical examination, electrocardiogram [ECG] parameters, and ECOG PS).

Exploratory Endpoints:
The exploratory endpoints include:
the duration of response according to RECIST 1.1,
the time to response according to RECIST 1.1 (time from randomization to the date of the first assessment demonstrating a CR or PR),
tumor shrinkage in target lesions per time point from Baseline,
PD-L1 expression levels in tumor cells and cells of the tumor microenvironment at baseline with their relation to selected clinical response parameters,
PK profile of Avelumab,
immunogenicity of Avelumab,
molecular, cellular, and soluble markers in peripheral blood and/or tumor tissue that may be relevant to the mechanism of action of, or response/resistance to Avelumab.

Key Inclusion Criteria:

Male or female subjects 18 years, with an ECOG PS of 0 to 1 at trial entry, with the availability of a formalin-fixed, paraffin-embedded block containing tumor tissue or 7 (preferably 10) unstained tumor slides with PD-L1+, at least 1 measurable tumor lesion, and with histologically confirmed metastatic or recurrent NSCLC. Subjects must not have received any treatment for systemic lung cancer, and have an estimated life expectancy of more than 12 weeks.

Key Exclusion Criteria:

Subjects whose disease harbors an activating EFGR mutation, or with non-squamous cell NSCLC whose disease harbors and anaplastic lymphoma kinase (ALK) rearrangement are not eligible. Other exclusion criteria include prior therapy with any antibody or drug targeting T-cell coregulatory proteins, concurrent anticancer treatment, or immunosuppressive agents, known severe hypersensitivity reactions to monoclonal antibodies (Grade 3 NCI-CTCAE v 4.03), history of anaphylaxis, or uncontrolled asthma (that is, 3 or more features of partially controlled asthma), and persisting toxicity related to prior therapy of Grade >1 NCI-CTCAE v 4.03 (except neuropathy). Subjects with brain metastases are excluded, except those meeting the following criteria: brain metastases that have been treated locally and have not been progressing at least 2 months after completion of therapy, do not require steroid maintenance therapy, and do not have ongoing neurological symptoms that are related to the brain localization of the disease.

Investigational Medicinal Product:

dose/mode of administration/dosing schedule: Avelumab will be administered as a 1-hour IV infusion at 10 mg/kg once every 2-weeks until progressive disease or unacceptable toxicity. In order to mitigate infusion-related reactions, all subjects will receive pretreatment with histamine H1 receptor (H1) blockers and acetaminophen 30 to 60 minutes prior to every Avelumab infusion. Premedication with an antihistamine and with paracetamol (acetaminophen) (for example, 25-50 mg diphenhydramine and 500-650 mg paracetamol [acetaminophen] IV or oral equivalent) approximately 30 to 60 minutes prior to each dose of Avelumab is mandatory. This regimen may be modified based on local treatment standards and guidelines as appropriate provided it does not include systemic corticosteroids.

Reference Therapy: Dose/Mode of Administration/Dosing Schedule:

Subjects randomized to chemotherapy will be administered the investigator-chosen chemotherapy regimen according to the protocol for up to a maximum of 6 cycles or until progressive disease or unacceptable toxicities. Dose adjustments can be made according to label instructions and local institutional practices.

Planned Trial and Treatment Duration Per Subject:

In this trial, treatment with Avelumab will continue until disease progression or unacceptable toxicity. Additionally, subjects receiving Avelumab who have experienced a CR should be treated for a maximum of 24 months after confirmation, at the discretion of the Investigator. Chemotherapy will be administered until disease progression or unacceptable toxicity or for a maximum of 6 cycles of chemotherapy.

Statistical Methods:

The primary endpoint for the trial, PFS time, will be analyzed in the ITT population using a one-sided stratified log-rank test at a significance level of 2.5% one-sided taking the randomization strata into account. Randomization will be stratified by histology (squamous/non-squamous). The analysis will be performed after 256 events have been observed, and a sample size of 420 subjects is planned. In case the analysis of PFS in the ITT population demonstrates the superiority of Avelumab versus platinum-based doublet, confirmatory analysis of PFS in the PD-L1++ subset of the ITT population, BOR, and OS, using a hierarchical test procedure are planned to control the overall significance level at 0.025 one-sided. Safety data will be summarized, and AEs will be summarized by incidence, severity, seriousness and relationship to trial drug.

EXAMPLE 4C

This example is about a phase Ib trial testing Avelumab in patients with advanced NSCLC. Patients with advanced NSCLC not previously treated systemically for metastatic or recurrent disease, without an activating EGFR mutation or ALK rearrangement, and not selected for PD-L1 expression were treated with Avelumab 10 mg/kg IV Q2W until progression, unacceptable toxicity, or withdrawal. Responses were evaluated every 6 weeks (RECIST 1.1). Adverse events (AEs) were graded by NCI-CTCAE v4.0. PD-L1 expression was assessed by IHC.

As of Oct. 23, 2015, 145 patients received Avelumab (median 10 weeks [range 2-30])). Median age was 70y (range 41-90), ECOG PS was 0 (31.0%) or 1 (69.0%), and histology was adenocarcinoma (63.4%), squamous (26.9%), other (3.4%), or unknown (6.2%). Treatment-related (TR) AEs occurred in 82 patients (56.6%; all grades); those occurring ≥10% were infusion-related reaction (IRR; 24 [16.6%]) and fatigue (21 [14.5%]). Grade ≥3 TRAEs were reported in 13 pts (9.0%); only IRR and fatigue occurred in >1 patient (each 3 [2.1%]). There were no treatment-related deaths. Among 75 patients with months f/u, unconfirmed ORR was 18.7% (95% CI: 10.6, 29.3) based on 1 CR and 13 PRs; 12 ongoing at cutoff. Stable disease was reported in 34 patients (45.3%); disease control rate was 64.0%. PD-L1 expression was evaluable in 45/75 patients (60.0%). Based on a ≥1% cutoff for tumor cell staining, 35/45 (77.8%) were PD-L1+ and ORR was 20.0% in PD-L1+(7/35; 95% CI: 8.4, 36.9) vs 0/10 (0.0, 30.8) in PD-L1– patients. Median PFS was 11.6 weeks (95% CI: 6.7, 17.9) for all treated patients.

Conclusions:

Single-agent Avelumab showed an acceptable safety profile and clinical activity in patients with NSCLC who were EGFR-wildtype and ALK-negative, not previously treated for advanced disease, and unselected for PD-L1 expression. A trend of higher ORR in PD-L1+ tumors is suggested.

EXAMPLE 5

High PD-L1 expression in mesothelioma patient tumor samples and tumor cells derived from malignant effusions, with the latter being induced by IFN-γ producing PD-1+ T cells indicates the prominent role of PD-1/PD-L1 pathway in maintaining an immunosuppressive milieu in mesothelioma.

This example is about a phase Ib trial testing Avelumab in patients with advanced, unresectable mesothelioma.

Patients received Avelumab at 10 mg/kg as a 1-h infusion Q2W until progression, confirmed complete response (CR), or unacceptable toxicity, or any criteria for withdrawal occurred. Tumors were assessed every 6 weeks (RECIST 1.1). A prespecified analysis of response was performed 13 weeks after first treatment of the 20th patient. Unconfirmed best overall response (BOR) and progression-free survival (PFS) were evaluated. Adverse events (AEs) were graded by NCI-CTCAE v4.0.

A total of 20 patients with histologically or cytologically confirmed unresectable mesothelioma (pleural or peritoneal) that progressed after prior platinum-pemetrexed-containing regimen or platinum-based regimen followed by pemetrexed were treated with Avelumab. As of 13 Feb. 2015, median duration of treatment was 12 weeks (range, 4-24), and 8 patients remained on treatment. Median age was 67y (range 32-84), ECOG performance status was 0 (15%) or 1 (85%), and patients had received a median of 2 prior treatments (range, 1-≥4). Histology was epithelial (65%), mixed (15%), or sarcomatoid (5%). Treatment-related treatment-emergent adverse events (TEAEs) of any grade occurred in 17 patients (85%); the most common (>10%) were infusion-related reactions (9 [45%]), fatigue (3 [15%]), pyrexia (3 [15%]), and pruritus (3 [15%]). Three patients (15%) experienced treatment-related grade ≥3 TEAEs (diarrhoea, colitis, decreased lymphocyte count, and increased blood creatine phosphokinase; each 1 event), and no treatment-related TEAEs had a fatal outcome. Objective responses were observed in 3 (15%) patients (95% CI: 3.2, 37.9); all were partial responses and ongoing at data cutoff. Stable disease (SD) was observed in 9 additional patients (45%). The overall disease control rate (PR plus SD) was 60.0% (12 out of 20 patients.) Median PFS by RECIST was 16.3 weeks (95% CI: 6.1, not estimable), and the PFS rate at 12 weeks was 66.7% (95% CI: 40.4, 83.4).

Conclusions:

Avelumab showed preliminary clinical activity in previously treated patients with advanced, unresectable mesothelioma who were not selected for tumor PD-L1 positivity and a manageable safety profile.

Update:

As of Oct. 23, 2015, 53 patients were treated with Avelumab. Median age was 66y (range 32-84), ECOG PS was 0 (26.4%) or 1 (73.6%), median number of prior treatments for LA/M disease was 1.5 (range 0-7). Histology was epithelial (81.1%), mixed (11.3%), sarcomatoid (3.8%), or unknown (3.8%). Treatment-related (TR) AEs occurred in 41 patients (77.4%); most common (>10%) were grade 1/2 infusion-related reaction (20 [37.7%]), fatigue (8 [15.1%]), chills (8 [15.1%]), and pyrexia (6 [11.3%]). Grade ≥3 TRAEs occurred in 4 patients (7.5%; colitis, decreased lymphocytes, and increased GGT or CPK [each 1 event]), and there were no treatment-related deaths. Unconfirmed ORR was 9.4% (5 PRs; 95% CI: 3.1, 20.7); 4 ongoing at cutoff. Stable disease was observed in 25 patients (47.2%); disease control rate was 56.6%. Median PFS was 17.1 weeks (95% CI: 6.1, 30.1), and PFS rate at 24 weeks was 38.4% (95% CI: 23.3, 53.4). Using a 5% cutoff for tumor cell staining, 14/39 evaluable (35.9%) were PD-L1+, ORR was 14.3% in PD-L1+(2/14) vs 8.0% in PD-L1− patients (2/25), and median PFS was 17.1 weeks (95% CI: 5.4, ne) in PD-L1+ vs 7.4 weeks (95% CI: 6.0, 30.1) in PD-L1− patients.

Conclusions:

Avelumab showed an acceptable safety profile and clinical activity in PD-L1+ and PD-L1− patients with advanced unresectable mesothelioma

EXAMPLE 6

This example is about a phase Ib trial testing Avelumab in patients with heavily pretreated, recurrent or refractory ovarian cancer.

75 women with recurrent or refractory stage III-IV ovarian cancer were treated with Avelumab. As of 13 Feb. 2015, median duration of treatment was 12 weeks (range, 2-54), and 8 patients remained on treatment. Median age was 62y (range 38-84), ECOG performance status was 0 [41.3%] or 1 [58.7%], and patients had received a median of 4 lines of prior treatment (range, 1-5). Treatment-related treatment-emergent adverse events (TEAEs) of any grade occurred in 52 patients (69.3%); the most common (>10%) were fatigue (12 [16.0%]), chills (9 [12.0%]), nausea (8 [10.7%]), and diarrhoea (8 [10.7%]). There were 6 patients (8.0%) reporting treatment-related grade 3/4 TEAEs (none occurred in more than 1 pt) and no treatment-related grade 5 TEAEs. Objective responses were observed in 8 (10.7%) patients (95% CI: 4.7, 19.9). All were partial responses and 5 (62.5%) were ongoing at data cutoff. Tumor shrinkage by 30% in target lesions was observed in 3 additional pts (4.0%); however, these patients did not meet criteria for response per investigator by RECIST criteria. Stable disease was observed in 33 additional patients (44.0%). Median PFS was 11.4 weeks (95% CI: 6.3, 12.0) and the PFS rate at 24 weeks was 17.2% (95% CI: 8.1, 29.2). Tumors were PD-L1+ in 74.6% of evaluable patients (n=67; 1% tumor expression cutoff). The ORR in PD-L1+ patients (n=50) was 12.0% and 5.9% in PD-L1− patients (n=17). OS data are immature at this time.

Conclusions:

Avelumab showed an acceptable safety profile and encouraging clinical activity in this largest-to-date cohort of patients with heavily pretreated, advanced ovarian cancer treated with anti-PD-(L)1 therapy. Analysis of PD-L1 expression shows a trend towards better response in PD-L1+ tumors.

EXAMPLE 7

This example is about a phase Ib trial, in second-line and switch maintenance settings (SwM), testing Avelumab in patients with advanced gastric or gastroesophageal junction cancer.

Patients received Avelumab at 10 mg/kg as a 1-h infusion Q2W until progression, confirmed complete response (CR), or unacceptable toxicity. Tumors were assessed every 6 weeks (RECIST 1.1). Unconfirmed best overall response (BOR) and progression-free survival (PFS) were evaluated. Adverse events (AEs) were graded by NCI-CTCAE v4.0.

As of 13 Feb. 2015, 75 patients with unresectable LA/M (locally advanced or metastatic GGEJC were treated with Avelumab: 20 patients in the 2L setting and 55 patients in the SwM group. The median follow-up time was 6 months (range 3-11) and median duration of treatment was 12 weeks (range 2-36). Median age was 57y (range 29-85), ECOG performance status was 0 (40%) or 1 (60%), and patients had received a median of 1 prior chemotherapy (range, 1-4). Treatment-related treatment-emergent adverse events (TE-AEs) of any grade occurred in 47 patients (62.7%); the most common (>9%) were infusion-related reactions (12 [16.0%]), nausea (7 [9.3%]), increased AST (7 [9.3%]), and increased ALT (7 [9.3%]). There were 9 patients (12.0%) reporting a treatment-related grade ≥3 TEAE; the most frequent were fatigue, thrombocytopaenia, and anaemia (each in 2 patients [2.7%]). There was 1 treatment-related grade 5 TEAE (hepatic failure in association with autoimmune hepatitis). Among 2L patients, response rate (ORR) was 15% (3 of 20 patients; 95% CI: 3.2, 37.9; all 3 partial responses [PR]; 1 ongoing at cutoff). In the SwM population, ORR was 7.3% (4 of 55 patients; 95% CI, 2.0, 17.6; 1 CR, 3 PR; 3 ongoing at cutoff). Stable disease (SD) was observed in 7 additional 2L patients (35.0%) and 26 additional SwM patients (47.3%). Median PFS duration and PFS rate at 24 weeks were 11.6 weeks (95% CI: 6.0, 21.9) and 19.3% (95% CI: 3.7, 44.1), respectively, for 2L patients. In the SwM group, these values were 14.1 weeks (9.9, 18.0) and 34.0% (19.8, 48.6).

Conclusions:

Avelumab showed a manageable safety profile in both 2L and SwM settings. Objective responses and disease stabilization were observed in both groups, who were unselected based on levels of PD-L1 expression.

EXAMPLE 8

This example is about a phase Ib trial testing Avelumab in patients with metastatic urothelial carcinoma.

Patients unselected for PD-L1 expression received Avelumab at 10 mg/kg Q2W as a 1-h infusion until confirmed progression, unacceptable toxicity, or any criterion for withdrawal occurred. Tumors were assessed every 6 weeks (RECIST 1.1). Best overall response and progression-free survival (PFS) were evaluated. Adverse events (AEs) were graded by NCI-CTCAE v4.0. PD-L1 expression was assessed by immunohistochemistry using various cutoff criteria.

As of 19 Mar. 2015, 44 patients with UC were treated with Avelumab (median 13 weeks [range 2-28]) and followed for a median of 3.5 months (range 3.0-5.0). Median age was 68y (range 30-84), ECOG performance status was 0 (43.2%) or 1 (56.8%), and all had received a median of 2 prior therapies (range 1-≥4). Treatment-related treatment-emergent AEs (TR-TEAEs) of any grade occurred in 26 pts (59.1%); those occurring ≥10% were infusion-related reactions (8 [18.2%]) and fatigue (7 [15.9%]). No treatment-related death occurred; 1 grade TR-TEAE (asthenia) was observed. Overall ORR was 15.9% (7 patients; 95% CI: 6.6, 30.1) with 1 CR and 6 PRs; 6 responses were ongoing at cutoff. Stable disease was observed in 19 pts (42.3%) and disease-control rate was 59.1%. PD-L1 expression was evaluable in 32 patients, including 6 of 7 responders. Using a ≥5%/≥1-intensity cutoff (≥5 of tumor cells show staining of any intensity (≥1+)), ORR was 40.0% in PD-L1+ pts (4/10) vs 9.1% in PD-L1− patients (2/22; p=0.060). PFS at 12 weeks was 70.0% (95% CI: 32.9, 89.2) in PD-L1+ tumors vs 45.5% (95% CI 22.7, 65.8) in PD-L1− tumors.

Conclusions: Avelumab showed an acceptable safety profile and had clinical activity in patients with UC. In patients with PD-L1+ tumors, there was a trend of higher ORR and longer PFS at 12 weeks.

EXAMPLE 9

This example is about a phase Ib trial testing Avelumab in patients with locally advanced or metastatic breast cancer (MBC), refractory to or progressing after standard-of-care therapy.

Patients received Avelumab at 10 mg/kg Q2W until confirmed progression, unacceptable toxicity, or any criterion for withdrawal occurred. Tumors were assessed every 6 weeks (RECIST 1.1). Unconfirmed best overall response was evaluated. Adverse events (AEs) were graded by NCI-CTCAE v4.0. Biopsy or surgical specimens were collected within 90 days prior to $1^{st}$ dose of Avelumab for biomarker analyses. Tumor PD-L1 expression was assessed by immunohistochemistry using various cutoff criteria.

As of 27 Feb. 2015, 168 patients (167 female, 1 male) with MBC, including ductal (56.5%), carcinoma NOS (9.5%), lobular (3.6%), or other (30.4%), were treated with Avelumab and followed for a median of 10 months (range 6-15). Median age was 55y (range 31-81), ECOG performance status was 0 (49.4%) or 1 (50.6%), and patients had received a median of 3 prior therapies for LA disease (range 0-10; patients must have received prior treatment with taxane and anthracycline, unless contraindicated). Patients were HER2−/ER+ or PR+(69 [41.1%]), triple negative (TNBC=HER2−/ER−/PR−; 57 [33.9%]), HER2+(26 [15.5%]), or had unknown biomarker status (16 [9.5%]). Median duration of treatment was 8 weeks (range, 2-50), and 9 patients (5.4%) remained on Avelumab. Any grade treatment-related treatment-emergent AEs (TEAEs) occurred in 120 patients (71.4%); the most common (>10%) were fatigue (33 [19.6%]), nausea (24 [14.3%]), and infusion-related reactions (20 [11.9%]). Treatment-related grade ≥3 TEAEs occurred in 24 patients (14.3%) and included (≥1%) fatigue, anemia, increased GGT, and autoimmune hepatitis (each 3 [1.8%]), and arthralgia (2 [1.2%]). There were 2 treatment-related deaths (acute liver failure, respiratory distress). Unconfirmed objective response rate (ORR) in the entire cohort was 5.4% (9 patients; 95% CI: 2.5, 9.9), with 1 CR and 8 PRs. Five of 9 responses were ongoing at time of cutoff. Stable disease was observed in additional 40 patients (23.8%), for an overall disease control rate of 29.2%. Evidence of tumor reduction by ≥30%, was seen in 15 patients (8.9%). There were responders in all biomarker subgroups, including 5 PRs in TNBC (n=57 [8.8%; 95% CI: 2.9, 19.3]). PD-L1 expression was evaluable in 136 patients. Among all patients with PD-L1 expressing immune cells within the tumor, 33.3% (4 of 12) had PRs. In patients with TNBC who had PD-L1+ immune cells within the tumor, 44.4% (4 of 9) had PRs, compared with 2.6% (1 of 39) for TNBC and PD-L1-immune cells.

Conclusions:

Avelumab showed an acceptable safety profile and has clinical activity in a subset of patients with MBC. In patients with TNBC, presence of PD-L1 expressing immune cells within the tumor may be associated with clinical responses to Avelumab.

EXAMPLE 10

This example is about a multicenter, international, randomized, open-label phase III trial comparing maintenance therapy with Avelumab with continuation of first-line chemotherapy in subjects with unresectable, locally advanced or metastatic, adenocarcinoma of the stomach, or of the gastro-esophageal junction (GEJ). Approximately 629 subjects will be enrolled and receive a first-line therapy comprised of oxaliplatin and either 5-FU or capecitabine (induction phase) for 12 weeks.

Following the induction phase, subjects who experience a CR, PR, or SD after 12 weeks (approximately 440 subjects) will be randomized to receive either Avelumab or continuation of the same regimen of chemotherapy from the induction phase (maintenance phase).

The dose and schedule of the chemotherapy during the Induction Phase are as follows:
  Oxaliplatin at 85 mg/m2 IV on Day 1 with 5-FU at 2600 mg/m2 IV continuous infusion over 24 hours on Day 1 plus leucovorin 200 mg/m2 IV on Day 1, given every 2 weeks (for up to 12 weeks), or
  Oxaliplatin at 130 mg/m2 IV on Day 1 with capecitabine at 1000 mg/m2, twice daily for 2 weeks followed by a 1-week rest period given every 3 weeks (for up to 12 weeks) Upon completion of chemotherapy in the Induction Phase, subjects without disease progression (subjects with SD, PR, or CR) will be eligible for randomization to the Maintenance Phase where they will receive either Avelumab, or continue the same regimen of chemotherapy from the Induction Phase.

Treatment during the Maintenance Phase are as follows:
1. For subjects randomized to Avelumab: Avelumab will be given at a dose of 10 mg/kg as a 1 hour IV infusion once every 2 weeks
2. For subjects randomized to chemotherapy: continuation of the same regimen of oxaliplatin-fluoropyrimidine doublet as in the Induction Phase for 2 additional cycles:
  Upon completion of the oxaliplatin-fluoropyrimidine doublet during the Maintenance Phase, all patients will continue to receive Best Supportive Care (BSC)
  Patients may receive 51 monotherapy as maintenance after the 2 cycles of oxaliplatin-fluoropyrimidine doublet as long as 51 monotherapy is approved for use as Standard of Care (SOC) at the investigator's institution
  For patients receiving chemotherapy dose modifications after the starting dose are allowed if the continuation of the oxaliplatin-fluoropyrimidine doublet is prohibited by toxicity Subjects will return to the clinic at regular intervals for assessments. Tumor measurements by computed tomography (CT) scan or magnetic resonance imaging (MRI) will be performed every 6 weeks to determine response to treatment. Clinical decision making will be based on investigator assessment of the scans. However, a central imaging laboratory will be used to collect all CT/MRI scans and an independent review committee (IRC) will evaluate response using RECIST v1.1 for the purpose of the study endpoint.

Study treatment will continue until:

Disease progression

Significant clinical deterioration (clinical progression) by investigator's opinion Unacceptable toxicity by investigator's opinion, or Any criterion for withdrawal from the trial or trial treatment is fulfilled.

For subjects receiving Avelumab, treatment may continue past the initial determination of disease progression per RECIST version 1.1 as long the following criteria are met:

Investigator-assessed clinical benefit, without any rapid disease progression

Tolerance of trial treatment

Stable Eastern Cooperative Oncology Group (ECOG) performance status (PS=0 or 1)

Treatment beyond progression will not delay an imminent intervention to prevent serious complications of disease progression (for example, central nervous system metastases).

Subjects receiving Avelumab who have experienced a CR should be treated for a minimum of 12 months and/or until disease progression or unacceptable toxicity, after confirmation of response. In case a subject with a confirmed CR relapses after stopping treatment, but prior to the end of the trial, 1 re-initiation of treatment is allowed at the discretion of the Investigator and after agreement with the Medical Monitor. To be eligible for re-treatment, the subject must not have experienced any toxicity that led to treatment discontinuation of the initial Avelumab therapy. Subjects who re-initiate treatment will stay on trial and will be treated and monitored according to the protocol and the "until progression" schedule in the Schedule of Assessments. Subjects in the Maintenance Phase will receive trial treatment until progressive disease (PD) per RECIST v1.1, significant clinical deterioration (clinical progression), unacceptable toxicity, withdrawal of consent, or if any criterion for withdrawal from the trial or trial treatment is fulfilled.

On-study subject management will be based on Investigator assessments, while the study endpoints will be based on IRC assessments. Subjects will attend clinic visits at regular intervals to receive trial treatment and for efficacy and safety assessments. After completion of the Maintenance Phase, subjects will enter the Follow-up Phase.

Planned Number of Subjects:

Approximately 629 subjects are planned to enter the chemotherapy Induction Phase and 440 subjects are planned to be randomized into the Maintenance Phase.

Primary Endpoint:

The primary endpoint of the trial is OS, defined as the time (in months) from randomization to the date of death, regardless of the actual cause of the subject's death.

Secondary Endpoints:

The key secondary endpoints include PFS and Best Overall

Response (BOR) according to RECIST v1.1 as adjudicated by the IRC. Other secondary endpoints include subject-reported outcomes/quality of life (assessed by the EQ-5D-5L, EORTC QLQ-C30, and EORTC module QLQ-ST022 questionnaires).

Exploratory Endpoints:

Tumor shrinkage in target lesions at each time point from baseline

PD-L1 expression levels in tumor cells and cells of the tumor microenvironment at baseline with their relation to selected clinical response parameters Molecular, cellular and soluble markers in peripheral blood and/or tumor tissue that may be relevant to the mechanism of action of, or response/resistance to Avelumab Duration of response of Avelumab Time to response of Avelumab Population PK of Avelumab and individual drug exposures based on sparse PK sampling Exposure response (exposure safety and exposure efficacy) for Avelumab with respect to selected safety and efficacy endpoints Immunogenicity of Avelumab.

Safety Endpoints:

Safety endpoints include adverse events (AEs), assessed throughout the trial and evaluated using the National Cancer Institute (NCI) Common Terminology Criteria for Adverse Events (CTCAE) v4.03, physical examinations, clinical laboratory assessments, concomitant medications, vital signs, electrocardiogram parameters, and ECOG PS.

Key Inclusion Criteria:

Male or female subjects aged ≥18 years, with an ECOG PS of 0 to 1 at trial entry, with the availability of a formalin-fixed, paraffin-embedded block containing tumor tissue or a minimum of 7 (preferably 10) unstained tumor slides suitable for PD-L1 expression assessment, at least 1 measurable tumor lesion, and with histologically confirmed unresectable, locally advanced or metastatic, adenocarcinoma of the stomach or the GEJ.

Key Exclusion Criteria:

Prior therapy with any antibody or drug targeting T-cell coregulatory proteins, concurrent anticancer treatment, or immunosuppressive agents. Other exclusion criteria include severe hypersensitivity reactions to monoclonal antibodies (Grade clusion criteria include history of anaphylaxis or uncontrolled asthma (that is, 3 or more features of partially controlled asthma), persisting toxicity related to prior therapy of Grade re featurTCAE v4.03 and prior chemotherapy for unresectable locally advanced or metastatic adenocarcinoma of the stomach or GEJ.

Investigational Medicinal Product: Dose/Mode of Administration/Dosing Schedule:

Avelumab will be administered as a 1-hour IV infusion at 10 mg/kg once every 2-week treatment cycle until PD or unacceptable toxicity. In order to mitigate infusion-related reactions, subjects will receive pretreatment with histamine H1 receptor (H1) blockers and acetaminophen 30 to 60 minutes prior to every Avelumab infusion. Premedication with an antihistamine and with paracetamol (acetaminophen) approximately 30 to 60 minutes prior to each dose of Avelumab is mandatory (for example, 25 to 50 mg diphenhydramine and 500 to 650 mg paracetamol [acetaminophen] IV or oral equivalent). This regimen may be modified based on local treatment standards and guidelines as appropriate provided it does not include systemic corticosteroids and has to be recorded as concomitant medication.

Reference Therapy:

Chemotherapy during the Maintenance Phase will be administered according to the following rules:

1. For subjects randomized to Avelumab: Avelumab will be given at a dose of 10 mg/kg as a 1 hour IV infusion once every 2 weeks 2. For subjects randomized to chemotherapy: continuation of the same regimen of oxaliplatin-fluoropyrimidine doublet as in the Induction Phase for 2 additional cycles:

Upon completion of the oxaliplatin-fluoropyrimidine doublet during the Maintenance Phase, all patients will continue to receive BSC Patients may receive S1 monotherapy as maintenance after the 2 cycles of
oxaliplatin-fluoropyrimidine doublet as long as S1 monotherapy is approved for use as SOC at the investigator's institution
For patients receiving chemotherapy dose modifications after the starting dose are allowed if the continuation of the oxaliplatin-fluoropyrimidine doublet is prohibited by toxicity
Therapy will be administered until disease progression, unacceptable toxicity, or for the accepted maximal duration of the agent(s) selected.

Planned Trial and Treatment Duration Per Subject:

In this trial, treatment with chemotherapy during the Induction Phase will last for 12 weeks, followed by the Maintenance Phase with either Avelumab or continuation of the same regimen of chemotherapy from the Induction Phase, which will continue until disease progression or unacceptable toxicity. Subjects receiving Avelumab who have experienced a CR should be treated for a minimum of 12 months and/or until disease progression or unacceptable toxicity, after confirmation of response.

Statistical Methods:

The primary endpoint is OS and will be considered as confirmatory evidence of efficacy. The primary analysis set will be the ITT Analysis Set. The type I error rate for the primary endpoint (OS) and 2 key secondary endpoints (PFS and BOR) will be controlled at 2.5% (1-sided) level using a hierarchical testing procedure. Only if the test associated with the primary endpoint (OS) hypothesis is significant will the key secondary endpoint PFS be tested. Similarly, only if the test associated with the key secondary endpoint PFS hypothesis is significant will the key secondary endpoint BOR be tested. The stratification factor will be region (Asia versus non-Asia).

Sample Size:

The sample size for this study is driven by the primary endpoint—OS. The study is event driven. The primary analysis on OS will be conducted after 336 deaths have occurred during the Maintenance Phase and Long Term Follow-Up Phase. There will also be an interim analysis for efficacy after 252 deaths (i.e. 75% of the planned maximum number of OS events) have been observed using a Lan-DeMets alpha spending function for O'Brien-Fleming efficacy boundary. With 336 deaths, the study provides ~90% power for the primary endpoint analysis. The nominal one-sided alpha levels are 0.0096 and 0.0221 for the interim and final analysis, respectively. Assuming approximately 70% of subjects enrolled in the Induction Phase will remain eligible for the Maintenance Phase after completing the Induction Phase, approximately 629 subjects will be enrolled in the Induction Phase, which results in 440 eligible subjects randomized in the Maintenance Phase to observe 336 OS events.

EXAMPLE 11

This example is about a phase III open-label, multicenter trial of Avelumab as a third-line treatment of unresectable, recurrent, or metastatic gastric or gastroesophageal junction adenocarcinoma. The purpose of this trial is to demonstrate superiority of therapy with Avelumab plus best supportive care versus physician's choice plus best supportive care chemotherapy.

Approximately 330 eligible patients not preselected for PD-L1 expression (ECOG performance status 0-1, histologically confirmed unresectable locally advanced or metastatic adenocarcinoma of the stomach or gastroesophageal junction [GEJ], fresh or archival tissue for PD-L1 expression assessment, 2 prior courses of systemic treatment for unresectable, recurrent or metastatic adenocarcinoma of the stomach or GEJ, no prior therapy with an antibody or drug targeting T cell coregulatory proteins, and no concurrent anticancer treatment or immunosuppressive agents, among other inclusion/exclusion criteria will be randomized to receive either BSC+Avelumab at a dose of 10 mg/kg as a 1 h intravenous infusion Q2W or BSC±chemotherapy (physician's choice of irinotecan [150 mg/m2] or paclitaxel [80 mg/m2] in patients eligible to receive chemotherapy). Patients not eligible for chemotherapy will receive BSC Q3W.

First Arm: Experimental: Avelumab+Best Supportive Care (BSC)

Avelumab will be administered as a 1-hour intravenous (IV) infusion at 10 milligram per kilogram (mg/kg) once every 2-week treatment cycle until confirmed progressive disease or unacceptable toxicity along with best supportive care (BSC). Best supportive care is defined as treatment administered with the intent to maximize Quality of life without a specific antineoplastic regimen and is based on investigator's discretion.

Second Arm: Active Comparator: Physician's Choice Chemotherapy

Physician's choice chemotherapy comprises of the following:
Paclitaxel+BSC or
Irinotecan+ BSC or
BSC alone: Subjects who are not deemed eligible to receive Paclitaxel or Irinotecan at the dose and schedule specified will receive BSC as per investigator discretion once every 3 weeks.

Irinotecan will be administered at a dose of 150 mg/m^2 on Day 1 and 15 of a 4-week treatment cycle until disease progression or unacceptable toxicities along with BSC. Paclitaxel will be administered at a dose of 80 mg/m^2 on Day 1, 8, and 15 of a 4-week treatment cycle until disease progression or unacceptable toxicities along with BSC. Best supportive care is defined as treatment administered with the intent to maximize Quality of life without a specific antineoplastic regimen and is based on investigator's discretion.

Outcome Measures:

1. Overall Survival: Time (in months) from randomization to the date of death, regardless of the actual cause of the subject's death.
2. Progression Free Survival (PFS): PFS is defined as the time from date of randomization until date of the first documentation of progressive disease (PD) or death due to any cause in the absence of documented PD, whichever occurs first. PFS will be assessed as per Response Evaluation Criteria in Solid Tumors version 1.1 (RECIST v1.1). PD is defined as at least a 20 percent (%) increase in the sum of longest diameter (SLD), taking as reference the smallest SLD recorded from baseline or the appearance of 1 or more new lesions.
3. Best Overall Response (BOR): BOR will be determined according to RECIST 1.1 and as adjudicated by an Independent Review Committee (IRC). BOR is defined as the best response of any of the complete response (CR), partial response (PR), stable disease (SD) and progressive disease (PD) recorded from the date of randomization until disease progression or recurrence (taking the smallest measurement recorded since the start of treatment as reference). CR: Disappearance of all evidence of target and non-target lesions. PR: At least 30% reduction from baseline in the sum of the longest diameter (SLD) of all lesions. Stable disease (SD)=Neither sufficient increase to qualify for PD nor sufficient shrinkage to qualify for PR. PD is defined as at least a 20 percent (%) increase in the SLD, taking as reference the smallest SLD recorded from baseline or the appearance of 1 or more new lesions.

4. Change from baseline in European Quality Of Life 5-dimensions (EQ-5D-5L) Health Outcome Questionnaire: The EQ-5D-5L Health Outcome Questionnaire is a measure of health status that provides a simple descriptive profile and a single index value. The EQ-5D-5L defines health in terms of mobility, self-care, usual activities, pain/discomfort and anxiety/depression. The 5 items are combined to generate health profiles. These profiles were converted to a continuous single index score using a one to one matching. The lowest possible score is −0.59 (unable to walk, unable to self-care, unable to do usual activities, extreme pain or discomfort, extreme anxiety or depression) and the highest is 1.00 (no problems in all 5 dimensions).

5. Change from baseline in European Organization for the Research and Treatment of Cancer Quality of Life (EORTC QLQ-C30) Global Health Status: EORTC QLQ-C30 is a 30-question tool used to assess the overall quality of life (QoL) in cancer subjects. It consists of 15 domains: 1 global health status (GHS) scale, 5 functional scales (Physical, role, cognitive, emotional, social), and 9 symptom scales/items (Fatigue, nausea and vomiting, pain, dyspnea, sleep disturbance, appetite loss, constipation, diarrhea, financial impact. The EORTC QLQ-C30 GHS/QoL score ranges from 0 to 100; High score indicates better GHS/QoL. Score 0 represents: very poor physical condition and QoL. Score 100 represents: excellent overall physical condition and QoL.

6. Change from baseline in European Organization for the Research and Treatment of Cancer Quality of Life Questionnaire-Stomach Cancer Specific (EORTC STO22) Questionnaire Scores: The QLQ-STO22 is a gastric cancer quality of life questionnaire. There are 22 questions concerning disease, treatment related symptoms, side effects, dysphagia, nutritional aspects, and questions about the emotional problems of gastric cancer (dysphagia, pain, reflux, eating restrictions, anxiety, dry mouth, body image, and hair loss). For the symptom scales or single items, participants will be assessed using a 4-point scale (1=not at all; 2=a little; 3=quite a bit; 4=very much). All scales and single-item scores ranged from 0 to 100. For the symptom scales or single items, a higher score indicated a high level of symptoms and problems, i.e. 0=no symptoms, 100=most severe symptoms.

Inclusion Criteria:
　Male or female subjects aged greater than or equal to (>=) 18 years
　Disease must be measurable by RECIST 1.1
　Subjects with histologically confirmed unresectable locally advanced or metastatic adenocarcinoma of the stomach or gastroesophageal junction (GEJ)
　Eastern Cooperative Oncology Group (ECOG) performance status (PS) of 0 to 1 at trial entry
　Estimated life expectancy of more than 12 weeks
　Adequate hematological, hepatic and renal functions defined by the protocol
　Negative blood pregnancy test at Screening for women of childbearing potential
　Effective contraception for both male and female subjects if the risk of conception exists Other protocol defined criteria could apply Exclusion Criteria:
　Prior therapy with any antibody or drug targeting T-cell coregulatory proteins
　Concurrent anticancer treatment
　Major surgery
　Subjects receiving immunosuppressive agents (such as steroids) for any reason should be tapered off these drugs before initiation of the trial treatment (with the exception of subjects with adrenal insufficiency, who may continue corticosteroids at physiologic replacement dose, equivalent to less than [<] 10 mg prednisone daily).
　All subjects with brain metastases, except those meeting the following criteria: a. Brain metastases have been treated locally, and b. No ongoing neurological symptoms that are related to the brain localization of the disease (sequelae that are a consequence of the treatment of the brain metastases are acceptable)
　Previous malignant disease (other than gastric cancer) within the last 5 years with the exception of basal or squamous cell carcinoma of the skin or carcinoma in situ (bladder, cervical, colorectal, breast)
　Prior organ transplantation, including allogeneic stem-cell transplantation Significant acute or chronic infections
　Active autoimmune disease that might deteriorate when receiving an immunostimulatory agent
　Known severe hypersensitivity reactions to monoclonal antibodies, any history of anaphylaxis, or uncontrolled asthma (that is, 3 or more features of partially controlled asthma)
　Persisting toxicity related to prior therapy except alopecia
　Neuropathy Grade greater than (>) 3
　Pregnancy or lactation
　Known alcohol or drug abuse
　History of uncontrolled intercurrent illness including hypertension, active infection, diabetes
　Clinically significant (i.e., active) cardiovascular disease
　All other significant diseases might impair the subject's tolerance of trial treatment
　Any psychiatric condition that would prohibit the understanding or rendering of informed consent and that would limit compliance with study requirements
　Vaccination within 4 weeks of the first dose of avelumab and while on trial is prohibited except for administration of inactivated vaccines
　Legal incapacity or limited legal capacity

EXAMPLE 12

This example is about a phase III, multicenter, multinational, randomized, open-label, parallel-arm study of Avelumab plus best supportive care (BSC) versus BSC alone as a maintenance treatment in patients with locally advanced or metastatic urothelial cancer whose disease did not progress after completion of first-line platinum-containing chemotherapy. The main purpose of this trial is to compare maintenance treatment with Avelumab plus best supportive care (BSC) with BSC alone, to determine if Avelumab has an effect on survival in patients with locally advanced or metastatic urothelial cancer that did not worsen during or following completion of firstline chemotherapy.

Primary Outcome Measures:
　Overall Survival: Overall survival is defined as the time from the date of randomization to the date of death due to any cause. Patients last known to be alive will be censored at date of last contact.

Secondary Outcome Measures:
  Progression-Free Survival (PFS): PFS is defined as the time from randomization to the date of the first documentation of objective progression of disease (PD) or death due to any cause, whichever occurs first.
  Objective Response (OR): Objective response is defined as a complete response (CR) or partial response (PR) according to RECIST v1.1 recorded from date of randomization until disease progression or death due to any cause.
  Duration of Response: Duration of response (DR) is defined, for patients with an objective response per RECIST v1.1, as the time from the first documentation of objective tumor response (CR or PR) to the first documentation of objective tumor progression or death due to any cause, whichever occurs first.
  Disease Control: Disease control (DC) is defined as CR, PR, or stable disease (SD) according to the RECIST v.1.1 recorded from randomization until disease progression or death due to any cause.
  Time to Deterioration (TTD): TTD is defined as the time from baseline to the first time the patient's score shows a 3 point or higher increase in the FACT Bladder Cancer Symptom Index Disease Related Symptoms subscale-Physical (FBISI-DRS-P).
  EuroQoL EQ-5D: Euro Quality of Life: 6 item patient completed questionnaire designed to assess health status in terms of a single index value or utility score. There are 2 components to the EuroQol EQ 5D: a Health State Profile which has individuals rate their level of problems (no, some or moderate, extreme) in 5 areas (mobility, self care, usual activities, pain/discomfort, and anxiety/depression) and a Visual Analogue Scale (VAS) in which patients rate their overall health status from 0 (worst imaginable) to 100 (best imaginable).
  Cmax: Cmax defined as the maximum plasma concentration of avelumab.
  Ctrough: Ctrough is defined as the trough plasma concentrate at the end of an avelumab dosing interval.
  Incidence of Anti-Drug Antibody (ADA): Percentage of patients receiving avelumab with positive ADA and neutralizing antibodies.
  Tumor Tissue Biomarkers: Analyses to evaluate candidate predictive biomarkers of sensitivity or resistance to avelumab, including but not limited to PD-L1 expression.
  Incidence of Adverse Events: The frequency of patients experiencing treatment emergent adverse events, graded according to the NCI CTCAE v4.03.
  Incidence of Laboratory Abnormalities: The frequency of patients with laboratory test abnormalities, graded according to the NCI CTCAE v4.03.
Other Pre-specified Outcome Measures:
  Antitumor Activity per irRECIST: Objective response and PFS will be assessed per immune-related response criteria (irRECIST).
  Estimated Enrollment: 668
  Arm A: Avelumab plus Best Supportive Care (BSC)
Biological/Vaccine: Avelumab
10 mg/kg as a 1 hour intravenous infusion every 2 weeks (Q2W) in 4 week cycles
Other: Best Supportive Care
  BSC will be administered as deemed appropriate by the treating physician, and could include treatment with antibiotics, nutritional support, correction of metabolic disorders, optimal symptom control and pain management (including palliative radiotherapy), etc. BSC does not include any active anti-tumor therapy, however local radiotherapy of isolated lesions with palliative intent is acceptable.
  Arm B: Best Supportive Care (BSC) alone
  Other: Best Supportive Care
  BSC will be administered as deemed appropriate by the treating physician, and could include treatment with antibiotics, nutritional support, correction of metabolic disorders, optimal symptom control and pain management (including palliative radiotherapy), etc. BSC does not include any active anti-tumor therapy, however local radiotherapy of isolated lesions with palliative intent is acceptable.

EXAMPLE 13

This example is about a phase Ib trial of Avelumab in Japanese patients with advanced gastric or gastroesophageal junction adenocarcinoma (GC/GEJ) based on level of PD-L1 expression. The purpose of this trial is to demonstrate safety and clinical activity.

Patients received Avelumab 10 mg/kg Q2W IV infusion until confirmed progression, unacceptable toxicity, or withdrawal. Tumors were assessed every 6 weeks (RECIST 1.1). Best overall response rate (ORR) and progression-free survival (PFS) were evaluated. Adverse events (AEs) were graded by NCI-CTCAE v4.0. PD-L1 expression on fresh tissue samples collected up to 6 months prior to trial and on archival samples was assessed by immunohistochemistry using various cutoff criteria. As of Mar. 11, 2015, 20 patients were treated with a median follow-up of 6 months. Treatment-related AEs (TRAEs) of any grade occurred in 18/20 patients (90%); 1 patient (5%) reported grade 3 TRAE (alanine aminotransferase increase). There were no treatment-related deaths. Confirmed ORR was 15.0% based on 3 partial responses (PR) and the disease control rate (PR+ stable disease) was 65.0%. Based on a ≥1% cutoff for tumor cell staining, patients with PD-L1+ samples (n=6 [30.0%]) showed a 50.0% ORR compared with no responses in patients with PD-L1− samples (n=14 [70.0%]). Median PFS was 12.3 weeks (95% CI: 3.1, ne) for PD-L1+ and 11.1 weeks (6.0, 12.1) for PD-L1− (also ≥1%, cutoff). PFS rate at 12 weeks was 66.7% (95% CI: 19.5, 90.4) and 32.1% (10.2, 56.9) for PD-L1+ and PD-L1− patients, respectively. No PD-L1-positivity was observed on infiltrating immune cells within the tumor (≥10% cutoff).

Conclusions:

Single agent Avelumab showed an acceptable safety profile and clinical activity in GC/GEJ patients. A trend of higher ORR was observed in PD-L1+ patients compared with PD-L1− in this small cohort. Analysis is ongoing and expansion of this cohort to 40 patients is underway.

EXAMPLE 14

This example is about a phase I trial of Avelumab in advanced thymic epithelial tumors (TETs, thymoma). The purpose of this trial is to demonstrate safety and efficacy in patients with relapsed TETs enrolled in a phase I trial.

Eligibility criteria: More than one prior standard therapy, no prior immune checkpoint inhibitors, no history of autoimmune (AI) disease. Treatment: Av 10-20 mg/kg infusion over 1 hr q2 weeks until progression or unacceptable toxicity. Responses were assessed q6 weeks by immune-related RECIST 1.1. Correlative studies: PD-1, PD-L1 IHC in tumor samples and peripheral blood immune subset analysis.

7 patients with thymoma (T; 1 B1, 3 B2, 2 B3, 1 B2/B3) and 1 with thymic carcinoma (TC) were enrolled. Median age 53 yrs (39-76). 3 patients with T (2 B3, 1 B2/B3) received Av 20 mg/kg and 4 T (1 B1, 3 B2) and 1 TC received Av 10 mg/kg. Responses: 4 (57%) patients with T had a PR (2 at 20 mg/kg, 2 at 10 mg/kg), 2 (29%) SD and 1 (14%) PD; 1 patient with TC had SD. In 3 of 4 patients with PR, response was observed after 1 dose of Av. Treatment-related adverse event (AE, all grades) in >15% patients were AI disorder in 5 (63%) patients and fatigue in 4 (50%) patients. Grade >3 AEs were AI disorder (G3 in 3 (38%) patients; G4 in 2 (25%) patients) and hypokalemia (G4 in 1 (13%) patient). AI AEs included 1 or more of the following: muscle weakness, myalgia, myositis, respiratory muscle insufficiency, hoarseness, paresthesia, dysphagia, dyspnea, diarrhea and elevated creatine kinase. AI AEs were rapidly and completely reversible with oral steroids in 3 patients; incompletely resolved with oral steroids in 1 patient, and gradually resolved with additional medications (IVIG, cyclosporine A) in 1 patient. All responders experienced AI AEs (myositis in 3 patients, all after a single dose of Av and enteritis in 1 patient) and response was seen before or shortly after start of steroids in 3 patients suggesting response was related to Av. Reduced CTLA4+ regulatory T cells and a decrease in the ratio of granulocytic myeloid-derived suppressor cells (MDSCs) vs. monocytic MDSCs was seen after treatment.

Conclusions:

Avelumab is active in thymoma. Response is accompanied by development of AI AEs which are generally reversible with oral steroids.

EXAMPLE 15

This example is about a phase III global, multicenter trial of a maintenance therapy with Avelumab versus continuation of first-line chemotherapy in patients with unresectable, locally advanced or metastatic gastric cancer.

The primary objective of this global, multicenter, open-label trial is to demonstrate superiority, defined by overall survival or progression-free survival, of maintenance therapy with Avelumab vs continuation of 1L chemotherapy. Approximately 666 eligible patients will receive induction chemotherapy and upon completion, approximately 466 patients without disease progression will be randomized to receive treatment in the maintenance phase.

Main eligibility criteria include: histologically confirmed unresectable locally advanced or metastatic (LA/M) adenocarcinoma of the stomach or gastroesophageal junction (AS/GEJ), ECOG PS 0-1, no prior chemotherapy for LA/M disease, no prior therapy with any drug targeting T cell coregulatory proteins, and no concurrent anticancer treatment or immunosuppressive agents. Patients are not preselected for PD-L1 expression; HER2+ patients are excluded.

During the induction phase, patients receive chemotherapy (oxaliplatin+5-fluorouracil+ leucovorin or oxaliplatin+ capecitabine) for 12 weeks. Patients entering the maintenance phase are randomized to receive either Avelumab 10 mg/kg as a 1 h intravenous infusion Q2W or continuation of 1L chemotherapy.

Treatment is given until disease progression, unacceptable toxicity, or consent withdrawal. Secondary endpoints include best overall response, quality of life (assessed via EQ-5D-5L, EORTC QLQ-C30, and EORTC QLQ-ST022), safety as per NCI-CTCAE v4.03, and tumor biomarkers. Responses are evaluated according to RECIST 1.1 and adjudicated by a blinded independent review committee. Trial enrollment began in December 2015.

EXAMPLE 16

This example is about a phase III global, multicenter, randomized, open-label trial of Avelumab versus docetaxel as second-line treatment for stage IIIb/IV or recurrent non-small-cell lung cancer.

The primary objective of the trial is to demonstrate superiority, defined by overall survival, of Avelumab vs docetaxel in patients with locally advanced unresectable, metastatic, or recurrent NSCLC whose disease has progressed following treatment with a platinum-containing doublet, and whose tumors express PD-L1 (primary analysis population). Approximately 650 patients will be randomized.

Eligibility criteria include: histologically confirmed NSCLC, fresh or archival tumor tissue for assessment of PD-L1 expression, known-negative EGFR mutation/ALK rearrangement status, and ECOG performance status 0-1. Patients receive either Avelumab 10 mg/kg IV Q2W or docetaxel at a starting dose of 75 mg/m$^2$ (per label) IV Q3W. Patients are stratified according to PD-L1 status and NSCLC histology (squamous vs non-squamous).

Treatment is given until disease progression, unacceptable toxicity, or consent withdrawal.

Secondary endpoints include progression-free survival, objective response rate, quality of life (assessed via EQ-5D, EORTC QLQ-C30, and QLQ-LC13), and safety as per NCI-CTCAE v4.03. Responses are evaluated according to RECIST 1.1 and adjudicated by a blinded independent endpoint review committee. Patients treated with docetaxel may not crossover to the Avelumab arm while the primary endpoint has not been met in planned analyses. Trial enrollment began in April 2015.

EXAMPLE 17

This example is about a phase Ib trial testing Avelumab in patients with metastatic adrenocortical carcinoma.

Patients with mACC who had progressed after platinum-based therapy and were unselected for PD-L1 expression were treated with Avelumab at 10 mg/kg IV Q2W until progression, unacceptable toxicity, or withdrawal. Prior and ongoing treatment with mitotane was permitted. Tumors were assessed every 6 weeks (RECIST 1.1). Objective response rate (ORR) and progression-free survival (PFS) were evaluated. Adverse events (AEs) were graded by NCI-CTCAE v4.0.

As of Oct. 23, 2015, 37 patients in the ITT population were treated with Avelumab (median 8 weeks [range 2-48]). Among all patients treated, median age was 50y (range 23-71), ECOG PS was 0 (37.8%) or 1 (62.2%), and median number of prior treatments for metastatic disease was 1 (range 0-5). Treatment-related (TR) AEs occurred in 23 patients (62.2%); the most common (>10%) were grade 1/2 nausea (6 [16.2%]), fatigue (5 [13.5%]), pyrexia (5 [13.5%]), and infusion-related reaction (5 [13.5%]). Grade ≥3 TRAEs occurred in 5 patients (13.5%; each 1 event): hyperkalemia, increased ALT, GGT, or transaminase, sepsis, spinal cord infection, and pneumonitis. Potential immune-related TRAEs occurred in 4 patients (10.8%), including 1 patient with grade 3 pneumonitis that resolved. There were no treatment-related deaths. Among 19 patients with ≥13 weeks f/u, unconfirmed ORR was 10.5% (2 PRs; 95% CI: 1.3, 33.1). Stable disease (SD) was observed in 5 patients (26.3%); disease control rate was 36.8% (7/19). Median PFS was 7.6 weeks (95% CI: 5.9, 23.9), and PFS rate at 12 weeks was 30.3% (95% CI: 12.3, 50.7).

Conclusions:
Avelumab showed an acceptable safety profile and clinical activity in patients with mACC, a dataset representing the first study to date of an anti-PD-(L)1 agent in this rare tumor type.

---

The invention claimed is:

1. A method of treating non-small cell lung cancer in a subject, comprising administering to the subject a therapeutically effective amount of an inhibitor of the interaction between the PD-1 receptor and its ligand PD-L1, wherein the inhibitor is an anti-PD-L1 antibody comprising in its heavy chain the three complementarity determining regions (CDRs) according to SEQ ID NOs: 1, 2 and 3, and in its light chain the three CDRs according to SEQ ID NOs: 4, 5 and 6, and wherein the subject has not previously received therapy for metastatic or recurrent disease.

2. The method according to claim 1, wherein the subject is human, the PD-1 receptor is human PD-1 receptor, and PD-L1 is human PD-L1.

3. The method according to claim 1, wherein the cancer is identified as a PD-L1 positive cancer.

4. The method according to claim 1, wherein the anti-PD-L 1 antibody is Avelumab, having the heavy chain sequences according to SEQ ID NOs: 7 or 8, and the light chain sequence according to SEQ ID NO: 9.

5. The method according to claim 4, wherein the anti-PD-L1 antibody is administered at a dose of 10 mg/kg body weight every other week.

6. The method according to claim 5, wherein the anti-PD-L1 antibody is administered as an intravenous infusion.

7. The method according to claim 6, wherein the anti-PD-L1 antibody is administered as a one hour intravenous infusion.

8. The method according to claim 1, wherein the method results in an objective complete response.

9. The method according to claim 1, wherein the method results in an objective partial response.

* * * * *